US008258973B2

(12) United States Patent
Newkirk

(10) Patent No.: US 8,258,973 B2
(45) Date of Patent: Sep. 4, 2012

(54) TRANSFERABLE PATIENT CARE EQUIPMENT SUPPORT

(75) Inventor: David C. Newkirk, Lawrenceburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 13/021,803

(22) Filed: Feb. 7, 2011

(65) Prior Publication Data

US 2011/0131057 A1    Jun. 2, 2011

Related U.S. Application Data

(62) Division of application No. 11/340,982, filed on Jan. 27, 2006, now Pat. No. 7,884,735.

(60) Provisional application No. 60/652,304, filed on Feb. 11, 2005.

(51) Int. Cl.
  G08B 3/00      (2006.01)
  G08B 13/00     (2006.01)
  A47C 17/00     (2006.01)
  H05K 1/00      (2006.01)
  G06Q 10/00     (2006.01)

(52) U.S. Cl. ............ 340/691.6; 705/2; 5/658; 439/76.1; 340/573.1

(58) Field of Classification Search ............... 340/591.6; 5/658; 439/76.1
See application file for complete search history.

(56) References Cited

U.S. PATENT DOCUMENTS

| 383,815 | A | 5/1888 | Kilborn |
|---|---|---|---|
| 1,290,809 | A | 1/1919 | Truax |
| 1,490,650 | A | 4/1924 | Wagner |
| 1,919,114 | A | 7/1933 | Ley |
| 2,470,524 | A | 5/1949 | Scudder |
| 2,497,425 | A | 2/1950 | Terry |
| 2,673,771 | A | 3/1954 | Krewson |
| 2,696,963 | A | 12/1954 | Sheperd |
| 2,740,873 | A | 4/1956 | Cronk |
| 2,858,421 | A | 10/1958 | Touvet |
| 3,004,743 | A | 10/1961 | Wenger |
| 3,213,877 | A | 10/1965 | May et al. |
| 3,431,937 | A | 3/1969 | Hettlinger et al. |
| 3,552,577 | A | 1/1971 | Latham, Jr. |
| 3,674,294 | A | 7/1972 | Kirkham |

(Continued)

FOREIGN PATENT DOCUMENTS

DE    197 01 603    7/1998

(Continued)

OTHER PUBLICATIONS

Pump Star User's Manual, The Headwall Company, Modular Services Company, Dec. 22, 2005, 11 pages.

(Continued)

*Primary Examiner* — George Bugg
*Assistant Examiner* — Jack Wang
(74) *Attorney, Agent, or Firm* — Barnes & Thornburg LLP

(57) ABSTRACT

A patient care equipment support includes power and data connectors configured to be coupled to power and data connectors of patient care equipment when the patient care equipment is coupled to the equipment support to provide a power coupling and a data coupling between the patient care equipment and the equipment support. The equipment support is transferable between a first device, such as a hospital bed, and a second device, such as an overhead support arm.

23 Claims, 20 Drawing Sheets

U.S. PATENT DOCUMENTS

| | | |
|---|---|---|
| 3,709,556 A | 1/1973 | Allard et al. |
| 3,814,023 A | 6/1974 | Stantial |
| 3,953,933 A | 5/1976 | Goldstein |
| 3,987,928 A | 10/1976 | Mori |
| 4,005,844 A | 2/1977 | Richmond |
| 4,094,484 A | 6/1978 | Galione |
| 4,113,222 A | 9/1978 | Frinzel |
| 4,190,224 A | 2/1980 | LeBlanc et al. |
| 4,225,104 A | 9/1980 | Larson |
| 4,262,874 A | 4/1981 | Seigh |
| 260,816 A | 9/1981 | Zissimopoulos et al. |
| 4,339,104 A | 7/1982 | Weidman |
| 4,343,411 A | 8/1982 | Chesnut et al. |
| 4,378,014 A | 3/1983 | Elkow |
| 4,465,333 A | 8/1984 | Caserta et al. |
| 4,489,454 A | 12/1984 | Thompson |
| 4,511,157 A | 4/1985 | Wilt, Jr. |
| 4,511,158 A | 4/1985 | Varga et al. |
| 4,559,036 A | 12/1985 | Wunsch |
| 4,600,209 A | 7/1986 | Kerr, Jr. |
| 4,616,797 A | 10/1986 | Cramer |
| D289,604 S | 5/1987 | Gallant et al. |
| 4,678,264 A | 7/1987 | Bowen et al. |
| 4,691,397 A | 9/1987 | Netzer |
| 4,718,892 A | 1/1988 | Yung-Ho |
| 4,721,358 A | 1/1988 | Faber et al. |
| 4,725,027 A | 2/1988 | Bekanich |
| 4,729,576 A | 3/1988 | Roach |
| 4,738,369 A | 4/1988 | Desjardins |
| 4,744,536 A | 5/1988 | Bancalari |
| 4,756,706 A | 7/1988 | Kerns et al. |
| 4,767,168 A | 8/1988 | Grandy |
| 4,767,181 A | 8/1988 | McEowen |
| 4,795,122 A | 1/1989 | Petre |
| 4,835,343 A | 5/1989 | Graef et al. |
| 4,844,582 A | 7/1989 | Giannini |
| 4,879,798 A | 11/1989 | Petre |
| 4,892,279 A | 1/1990 | Lafferty et al. |
| 4,901,967 A | 2/1990 | Petre |
| 4,903,340 A | 2/1990 | Sorensen |
| 4,905,882 A | 3/1990 | Ross |
| 4,905,944 A | 3/1990 | Jost et al. |
| 4,924,349 A | 5/1990 | Buehler et al. |
| 4,925,444 A | 5/1990 | Orkin et al. |
| 4,945,592 A | 8/1990 | Sims et al. |
| 4,966,340 A | 10/1990 | Hunter |
| 4,969,768 A | 11/1990 | Young |
| 4,977,619 A | 12/1990 | Crimmins |
| 4,984,297 A | 1/1991 | Manome |
| 4,997,150 A | 3/1991 | Mardollo |
| 5,016,307 A | 5/1991 | Rebar |
| 5,026,017 A | 6/1991 | Kreuzer |
| 5,033,112 A | 7/1991 | Bowling et al. |
| 5,049,876 A | 9/1991 | Kahle et al. |
| 5,060,303 A | 10/1991 | Wilmoth |
| 5,073,681 A | 12/1991 | Hubben et al. |
| 5,078,349 A | 1/1992 | Smith |
| 5,083,807 A | 1/1992 | Bobb et al. |
| 5,089,974 A | 2/1992 | Demeyer et al. |
| 5,094,418 A | 3/1992 | McBarnes, Jr. et al. |
| 5,099,346 A | 3/1992 | Lee et al. |
| 5,103,108 A | 4/1992 | Crimmins |
| 5,107,636 A | 4/1992 | Schindele et al. |
| 5,108,064 A | 4/1992 | Kreuzer |
| 5,109,452 A | 4/1992 | Selvin et al. |
| 5,110,076 A | 5/1992 | Snyder et al. |
| 5,112,019 A | 5/1992 | Metzler et al. |
| 5,113,897 A | 5/1992 | Kummerfeld et al. |
| 5,117,521 A | 6/1992 | Foster et al. |
| 5,125,607 A | 6/1992 | Pryor |
| 5,135,191 A | 8/1992 | Schmuhl |
| 5,140,659 A | 8/1992 | Minds et al. |
| 5,146,528 A | 9/1992 | Gleim et al. |
| 5,149,036 A | 9/1992 | Sheehan |
| 5,180,886 A | 1/1993 | Dierenbach et al. |
| 5,207,642 A | 5/1993 | Orkin et al. |
| 5,212,760 A | 5/1993 | Goetz |
| 5,214,526 A | 5/1993 | Tonomura |
| 5,219,139 A | 6/1993 | Hertzler et al. |
| 5,224,681 A | 7/1993 | Lundstrom |
| 5,242,315 A | 9/1993 | O'Dea |
| 5,247,380 A | 9/1993 | Lee et al. |
| 5,274,490 A | 12/1993 | Tsushima et al. |
| 5,278,536 A | 1/1994 | Furtaw et al. |
| 5,305,132 A | 4/1994 | Fasen et al. |
| 5,305,133 A | 4/1994 | Cooper et al. |
| 5,306,109 A | 4/1994 | Kreuzer et al. |
| 5,319,816 A | 6/1994 | Ruehl |
| 5,321,542 A | 6/1994 | Freitas et al. |
| 5,326,059 A | 7/1994 | Pryor et al. |
| 5,337,992 A | 8/1994 | Pryor et al. |
| 5,344,169 A | 9/1994 | Pryor et al. |
| 5,366,191 A | 11/1994 | Bekanich |
| 5,400,995 A | 3/1995 | Boyd |
| 5,407,163 A | 4/1995 | Kramer et al. |
| 5,416,627 A | 5/1995 | Wilmoth |
| 5,421,548 A | 6/1995 | Bennett et al. |
| 5,452,807 A | 9/1995 | Foster et al. |
| 5,456,373 A | 10/1995 | Ford |
| 5,456,655 A | 10/1995 | Morris |
| 5,477,010 A | 12/1995 | Buckshaw et al. |
| 5,479,958 A | 1/1996 | Kummerfeld |
| 5,508,836 A | 4/1996 | DeCaro et al. |
| 5,527,125 A | 6/1996 | Kreuzer et al. |
| 5,548,654 A | 8/1996 | Fast |
| 5,556,065 A | 9/1996 | Wadley |
| 5,561,412 A | 10/1996 | Novak et al. |
| 5,579,001 A | 11/1996 | Dempsey et al. |
| 5,588,166 A | 12/1996 | Burnett |
| 5,594,786 A | 1/1997 | Chaco et al. |
| 5,596,648 A | 1/1997 | Fast |
| 5,617,236 A | 4/1997 | Wang et al. |
| 5,618,090 A | 4/1997 | Montague et al. |
| 5,636,823 A | 6/1997 | Boyd |
| 5,644,876 A | 7/1997 | Walker |
| 5,647,491 A | 7/1997 | Foster et al. |
| 5,657,201 A | 8/1997 | Kochis |
| 5,657,884 A | 8/1997 | Zilincar, III |
| 5,675,125 A | 10/1997 | Hollinger |
| 5,696,861 A | 12/1997 | Schimmeyer et al. |
| 5,699,038 A | 12/1997 | Ulrich et al. |
| 5,699,988 A | 12/1997 | Boettger et al. |
| 5,704,577 A | 1/1998 | Gordon |
| 5,706,110 A | 1/1998 | Nykanen |
| 5,723,817 A | 3/1998 | Arenas et al. |
| 5,811,729 A | 9/1998 | Rintz |
| 5,811,730 A | 9/1998 | Rintz |
| 5,813,873 A | 9/1998 | McBain et al. |
| 5,838,223 A | 11/1998 | Gallant et al. |
| 5,838,471 A | 11/1998 | Beard |
| 5,857,685 A | 1/1999 | Phillips et al. |
| 5,874,693 A | 2/1999 | Rintz |
| 5,876,016 A | 3/1999 | Urban et al. |
| 5,877,820 A | 3/1999 | Yamamuro et al. |
| 5,878,536 A | 3/1999 | Demmitt et al. |
| 5,895,888 A | 4/1999 | Arenas et al. |
| 5,898,961 A | 5/1999 | Ambach et al. |
| 5,907,419 A | 5/1999 | Martnelli et al. |
| 5,910,776 A | 6/1999 | Black |
| 5,924,658 A | 7/1999 | Shiery et al. |
| 5,949,567 A | 9/1999 | Jebens |
| 5,966,760 A | 10/1999 | Gallant et al. |
| 5,967,840 A | 10/1999 | Rose et al. |
| 5,982,519 A | 11/1999 | Martnelli et al. |
| 5,987,670 A | 11/1999 | Sims et al. |
| 5,994,998 A | 11/1999 | Fisher et al. |
| 5,995,253 A | 11/1999 | Flaherty |
| 5,998,735 A | 12/1999 | Patterson, Jr. |
| 6,051,787 A | 4/2000 | Rintz |
| 6,056,249 A | 5/2000 | Fillon, Jr. |
| 6,071,015 A | 6/2000 | Erbse et al. |
| 6,073,285 A | 6/2000 | Ambach et al. |
| 6,095,468 A | 8/2000 | Chirico et al. |
| 6,109,572 A | 8/2000 | Urban et al. |
| 6,117,076 A | 9/2000 | Cassidy |
| 6,140,911 A | 10/2000 | Fisher et al. |
| 6,147,592 A | 11/2000 | Ulrich et al. |

| Patent Number | Date | Inventor |
|---|---|---|
| 6,155,743 A | 12/2000 | Chen |
| 6,170,102 B1 | 1/2001 | Kreuzer |
| 6,179,260 B1 | 1/2001 | Ohanian |
| 6,182,662 B1 | 2/2001 | McGhee |
| 6,183,101 B1 | 2/2001 | Chien |
| 6,193,655 B1 | 2/2001 | McGrath |
| 6,201,983 B1 | 3/2001 | Haumann et al. |
| 6,213,481 B1 | 4/2001 | Marchese et al. |
| 6,231,016 B1 | 5/2001 | Slone |
| 6,259,355 B1 | 7/2001 | Chaco et al. |
| 6,281,440 B1 | 8/2001 | Baldwin et al. |
| 6,304,600 B1 | 10/2001 | Chiba |
| 6,329,906 B1 | 12/2001 | Fisher et al. |
| 6,349,436 B1 | 2/2002 | Kreuzer |
| 6,355,885 B1 | 3/2002 | Rintz et al. |
| 6,362,725 B1 | 3/2002 | Ulrich et al. |
| 6,375,133 B1 | 4/2002 | Morrow |
| 6,390,311 B1 | 5/2002 | Belokin |
| 6,434,187 B1 | 8/2002 | Beard et al. |
| 6,434,329 B1 | 8/2002 | Dube et al. |
| 6,442,145 B1 | 8/2002 | De Lange et al. |
| 6,445,299 B1 | 9/2002 | Rojas, Jr. |
| 6,457,874 B1 | 10/2002 | Clapp, Jr. et al. |
| 6,486,792 B1 | 11/2002 | Moster et al. |
| 6,493,121 B1 | 12/2002 | Althaus |
| 6,496,105 B2 | 12/2002 | Fisher et al. |
| 6,500,026 B2 | 12/2002 | Yamaguchi |
| 6,504,633 B1 | 1/2003 | Hovorka et al. |
| 6,504,635 B1 | 1/2003 | Nakashima |
| 6,514,652 B2 | 2/2003 | Cash, Jr. |
| 6,533,466 B1 | 3/2003 | Smith |
| 6,544,075 B1 | 4/2003 | Liao |
| 6,544,200 B1 | 4/2003 | Smith et al. |
| 6,545,218 B1 | 4/2003 | Blaess |
| 6,552,888 B2 | 4/2003 | Weinberger |
| 6,558,045 B2 | 5/2003 | Yamaguchi |
| 6,563,618 B1 | 5/2003 | Morrow et al. |
| 6,585,206 B2 | 7/2003 | Metz et al. |
| 6,585,431 B1 | 7/2003 | Okamoto |
| 6,599,025 B1 | 7/2003 | Deutsch |
| 6,601,860 B2 | 8/2003 | Potter |
| 6,608,253 B1 | 8/2003 | Rintz |
| 6,609,166 B1 | 8/2003 | Nakashima |
| 6,619,599 B2 | 9/2003 | Elliott et al. |
| 6,659,947 B1 | 12/2003 | Carter et al. |
| 6,668,328 B1 | 12/2003 | Bell |
| 6,668,493 B1 | 12/2003 | Walker |
| 6,688,779 B2 | 2/2004 | Nishita |
| 6,708,991 B1 | 3/2004 | Ortlieb |
| 6,725,483 B2 | 4/2004 | Gallant et al. |
| 6,763,195 B1 | 7/2004 | Willebrand et al. |
| 6,978,499 B2 | 12/2005 | Gallant et al. |
| 7,039,456 B2 | 5/2006 | Chen |
| 7,040,057 B2 | 5/2006 | Gallant et al. |
| 7,065,811 B2 | 6/2006 | Newkirk et al. |
| 7,065,812 B2 | 6/2006 | Newkirk et al. |
| 7,068,143 B2 | 6/2006 | Doering et al. |
| 7,150,655 B2 | 12/2006 | Mastrototaro et al. |
| 7,154,397 B2 | 12/2006 | Zerhusen et al. |
| 7,177,673 B2 | 2/2007 | Matsumura et al. |
| 7,219,472 B2 | 5/2007 | Gallant et al. |
| 7,244,150 B1 | 7/2007 | Brase et al. |
| 7,310,839 B2 | 12/2007 | Salvatini et al. |
| 7,399,205 B2 | 7/2008 | McNeely et al. |
| 7,884,735 B2 | 2/2011 | Newkirk |
| 2002/0004336 A1 | 1/2002 | Yamaguchi |
| 2002/0012329 A1 | 1/2002 | Atkinson et al. |
| 2002/0014951 A1 | 2/2002 | Kramer et al. |
| 2002/0021209 A1 | 2/2002 | Fisher et al. |
| 2002/0023121 A1 | 2/2002 | Sugiyama et al. |
| 2002/0032812 A1 | 3/2002 | Ito |
| 2002/0039068 A1 | 4/2002 | Holowick |
| 2002/0044059 A1 | 4/2002 | Reeder et al. |
| 2002/0060624 A1 | 5/2002 | Zhang |
| 2002/0067282 A1 | 6/2002 | Moskowitz et al. |
| 2002/0091843 A1 | 7/2002 | Vald |
| 2002/0101349 A1 | 8/2002 | Rojas, Jr. |
| 2002/0101861 A1 | 8/2002 | Gancarcik et al. |
| 2002/0142650 A1 | 10/2002 | Clark et al. |
| 2002/0149822 A1 | 10/2002 | Stroud |
| 2002/0152555 A1 * | 10/2002 | Gallant et al. ............ 5/658 |
| 2002/0179092 A1 | 12/2002 | Swennen et al. |
| 2002/0196141 A1 | 12/2002 | Boone et al. |
| 2003/0006881 A1 | 1/2003 | Reyes |
| 2003/0014817 A1 | 1/2003 | Gallant et al. |
| 2003/0016419 A1 | 1/2003 | Palmer et al. |
| 2003/0025601 A1 | 2/2003 | Gruteser et al. |
| 2003/0039257 A1 | 2/2003 | Manis et al. |
| 2003/0052770 A1 | 3/2003 | Mansfield, Jr. et al. |
| 2003/0052787 A1 | 3/2003 | Zerhusen et al. |
| 2003/0058085 A1 | 3/2003 | Fisher et al. |
| 2003/0062990 A1 | 4/2003 | Schaeffer, Jr. et al. |
| 2003/0062991 A1 | 4/2003 | Fisher et al. |
| 2003/0153387 A1 | 8/2003 | Small et al. |
| 2003/0185515 A1 | 10/2003 | Lubkert et al. |
| 2003/0223756 A1 | 12/2003 | Tatum et al. |
| 2003/0227900 A1 | 12/2003 | Watanabe |
| 2003/0230687 A1 | 12/2003 | Metz et al. |
| 2004/0019996 A1 | 2/2004 | Singer |
| 2004/0091270 A1 | 5/2004 | Choi et al. |
| 2004/0164220 A1 | 8/2004 | Newkirk |
| 2005/0000019 A1 | 1/2005 | Newkirk et al. |
| 2005/0007258 A1 | 1/2005 | Moster et al. |
| 2005/0017468 A1 | 1/2005 | Gallant et al. |
| 2005/0033124 A1 | 2/2005 | Kelly et al. |
| 2005/0253034 A1 | 11/2005 | Bally et al. |
| 2006/0179571 A1 | 8/2006 | Newkirk |
| 2007/0018058 A1 | 1/2007 | Graham et al. |
| 2007/0141869 A1 * | 6/2007 | McNeely et al. ............ 439/76.1 |
| 2009/0065668 A1 | 3/2009 | Walke |

FOREIGN PATENT DOCUMENTS

| | | |
|---|---|---|
| DE | 199 12 395 | 9/2000 |
| EP | 0 943 306 | 9/1999 |
| EP | 1 234 900 | 8/2002 |
| GB | 1 061 383 | 3/1967 |
| WO | WO 00/37978 | 1/2000 |
| WO | WO 00/09061 | 2/2000 |
| WO | WO 2005/022692 | 3/2005 |

OTHER PUBLICATIONS

"Modular Pump Star", The Headwall Company, Modular Services Company, 2005, 4 pages.

* cited by examiner

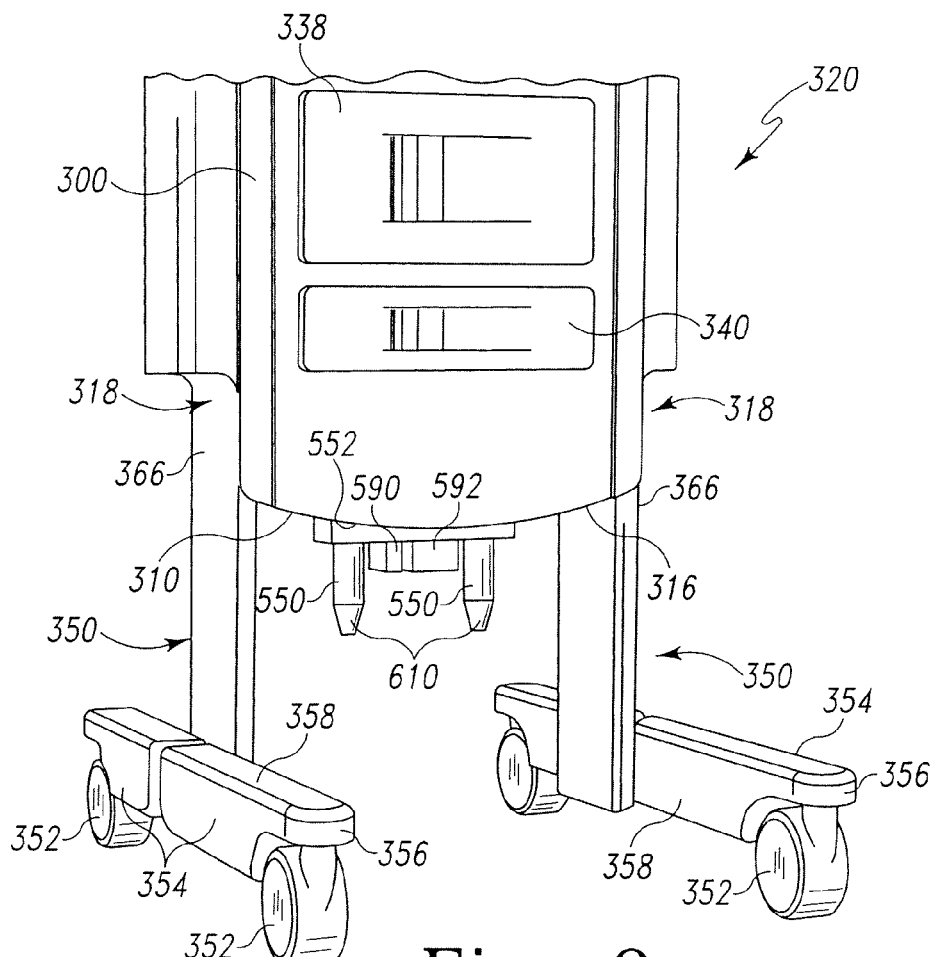
Fig. 9
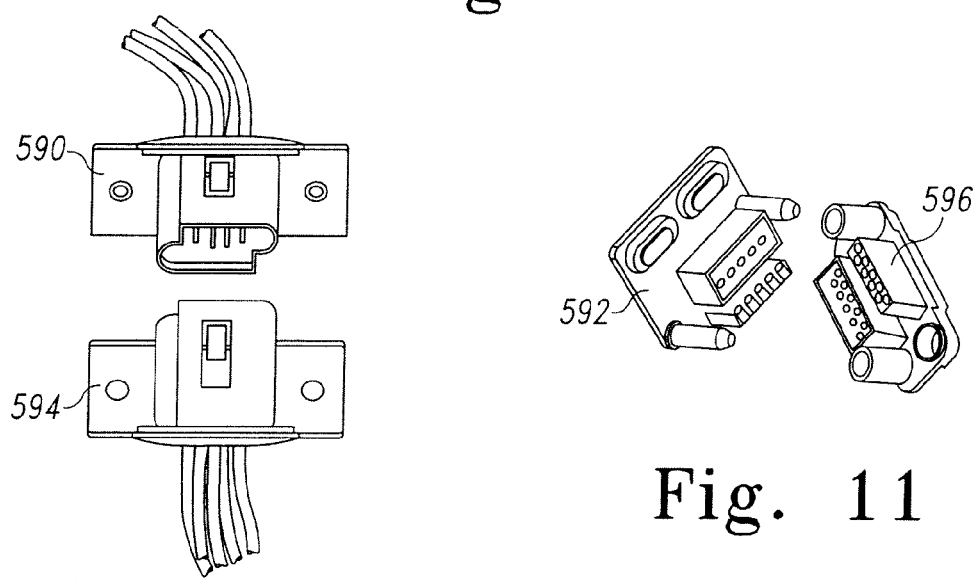
Fig. 10
Fig. 11

TRANSFERABLE PATIENT CARE EQUIPMENT SUPPORT

CROSS REFERENCE TO RELATED APPLICATIONS

This application is a divisional of U.S. application Ser. No. 11/340,982, filed on Jan. 27, 2006, now U.S. Pat. No. 7,884,735, which claimed the benefit of U.S. Provisional Patent Application, Ser. No. 60/652,304, filed on Feb. 11, 2005, and each of which is hereby incorporated by reference herein.

FIELD OF THE INVENTION

The present disclosure relates to a patient care equipment support, and more particularly relates to a patient care equipment support that is transferable between a first device, such as a hospital bed, and a second device, such as a support arm or a column.

BACKGROUND OF THE INVENTION

Hospitalized patients often require patient care equipment to be in close proximity during hospital care. Such patient care equipment is typically supported on a patient care equipment support or rack. Examples of patient care equipment include an infusion pump, a ventilator, a cardiac monitor, a pulse oximeter, a non-invasive blood pressure measuring device, a digital thermometer, a liquid oxygen module, a defibrillator, a respiratory rate measuring device, medical gas delivery equipment (such as an oxygen tank), intra-venous bags, and the like, many of which directly connect to the patient via lines or tubes.

Some supports carrying the patient care equipment are transferable between a patient support apparatus, such as a hospital bed, a stretcher, an ambulatory care chair, and the like, and another support structure, such as a ceiling or wall-mounted service column, a ceiling or wall-mounted equipment support arm, a floor-supported stand, a wheeled cart, a headwall, a wall of a hospital room, and the like.

SUMMARY OF THE INVENTION

The present invention comprises one or more of the following features or one or more of the elements in the appended claims or combinations thereof.

A patient care equipment support may include power and data connectors configured to be coupled to respective power and data connectors of patient care equipment when the patient care equipment is coupled to the equipment support to provide a power coupling and a data coupling between the patient care equipment and the equipment support.

The data coupling may be configured to transmit a control signal to the patient care equipment. The equipment support may include an on-board battery for supplying power to the patient care equipment.

The patient care equipment may include any one or more of the following: an infusion pump, a ventilator, a cardiac monitor, a pulse oximeter, a non-invasive blood pressure measuring device, a digital thermometer, a liquid oxygen module, an oxygen tank, a defibrillator, a respiratory rate measuring device, medical gas delivery equipment (such as an oxygen tank), intra-venous bags, and the like. The equipment support may further comprise any one or more of the following: a microcontroller, a user interface device, a display, and the like.

The equipment support may include a main structure and a pair of extendible support legs with floor-engaging wheels so that the equipment support may be decoupled from a first device, such as a hospital bed, and supported on an underlying floor. The support legs may retract relative to the main structure when the equipment support is lifted off the floor and coupled to the first device. Each of the support legs may include a first member that moves vertically relative to the main structure and a pair of second members pivotably coupled to a lower region of the first member. The wheels may be coupled to respective second members and the second members may pivot downwardly from respective storage positions in which the wheels are spaced from the floor to respective use positions in which the wheels contact the floor.

The equipment support may be transferable between a first device having first power and data connectors and a second device having second power and data connectors. The equipment support may have third power and data connectors and fourth power and data connectors. The equipment support may be configured to be detachably coupled to the first device so that the third power and data connectors couple to the respective first power and data connectors to supply power to the equipment support and to establish a communication link between the first device and the equipment support.

The equipment support may be configured to be detachably coupled to the second device so that the fourth power and data connectors couple to the respective second power and data connectors to supply power to the equipment support and to establish a communication link between the second device and the equipment support. The communication links between the first and second devices and the equipment support may be wired or wireless.

The third and the fourth power and data connectors may be arranged so that the first and second power and data connectors can be coupled substantially simultaneously to the respective third and fourth power and data connectors before disconnection of either one of the first and second power and data connectors from the respective third and fourth power and data connectors to permit the equipment support to be transferred between the first and second devices without a loss of power to the equipment support or without a loss of communication link with the equipment support.

The first and/or the second device may be a patient support apparatus, such as a hospital bed, a stretcher, a chair, a surgery table, an examination table, a wheel chair, and the like. The first and/or the second device may be a support structure, such as a support arm, a column, a service chase, a headwall, a cart, a stand, or any other piece of architectural equipment.

The equipment support may include at least one equipment-receiving cavity and the power and data connectors of the patient care equipment may couple automatically to the respective power and data connectors of the equipment support when the patient care equipment is inserted at least partially into the at least one equipment-receiving cavity. The at least one equipment-receiving cavity may comprise a plurality of equipment-receiving cavities. Each equipment-receiving cavity may be configured to receive the associated patient care equipment.

The power and data connectors of the equipment support and the patient care equipment may be drawer connectors to facilitate automatic blind mating when the patient care equipment is inserted into the associated equipment-receiving cavity of the equipment support. The power and data connectors of the equipment support may be receptacle connectors, and the power and data connectors of the patient care equipment may be plug connectors.

The patient support apparatus may comprise a base frame and an upper frame supported above the base frame. A support structure may extend outwardly from the base frame so that at least a portion of the support structure extends outside a footprint of the upper frame. The portion of the support structure extending outside the footprint of the upper frame may be configured to carry the equipment support such that the equipment support is spaced from an underlying floor. The equipment support may have an upper portion situated above the upper frame. The equipment support may be detachably coupled to the support structure.

An apparatus may comprise a hospital bed having movable portions, patient monitoring equipment coupled to the hospital bed to monitor at least one patient physiological condition, and a user interface device coupled to the hospital bed. The user interface device may include a display for displaying patient data and controls for controlling bed functions. The patient data may include one or more of the following: blood pressure, temperature, pulse rate, respiratory rate, blood oxygen saturation level, patient weight, and the like.

The user interface device may comprise a touchscreen display and/or buttons on a housing around a display screen. The touchscreen display may be operable to display patient data and a plurality of icons that are touchable to move the movable portions of the hospital bed. In some embodiments, the touchscreen display may be operable to the display the patient data and the plurality of icons at the same time. In other embodiments, the touchscreen display may be operable to display the patient data and the plurality of icons at different times. When buttons are provided on the housing around the display screen, the buttons may control dedicated functions of the hospital bed. In some embodiments, the functions associated with the buttons may change in connection with changes to the information shown on the display screen. In such embodiments, indicia regarding active functions currently associated with the buttons may be shown on the display screen near the buttons.

The hospital bed may include a detachable patient care equipment support. The touchscreen display may be coupled to the detachable equipment support. The equipment support may include a microcontroller coupled to the touchscreen display. The touchscreen display may be operable to display a plurality of icons that are touchable to provide input to the microcontroller.

The display may be configured to display the operational status of the hospital bed including information concerning one or more of the following: bed function lock-outs, bed articulation, bed elevation, siderail positions, and therapy surface data. The display may be configured to display the operational status of the patient care equipment including information concerning one or more of the following: an alarm status and equipment settings.

A power connector may include a wired coupler to supply electrical power to the patient care equipment. A data connector may include a wired or wireless coupler to establish a communication link between the patient care equipment and the equipment support. A wired coupler may include electrical contacts. A wireless coupler may include one or more of the following: a photoemitter, a photodetector, a photodiode, a radio frequency (RF) transmitter, an RF receiver, an RF transceiver, an infrared (IR) transmitter, an IR receiver, and an IR transceiver.

Data from the patient care equipment may be wirelessly communicated to the equipment support from, and/or wirelessly communicated from the equipment support to, a computer network of a healthcare system. The wireless communication may be in accordance with any desired protocol, including the following protocols: IrDA, spread spectrum (including the Bluetooth protocol), RS232, TCP/IP, USB, and 802.11$_x$. The wireless communication may use frequency modulation or frequency modulated infrared (FMIR).

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures, in which:

FIG. 9 is a perspective view of a lower portion of the equipment support showing a pair of coupling pins, a power connector and a data connector extending downwardly from a downwardly-facing wall of the equipment support;

FIG. 10 a perspective view of a power connector of the equipment support;

FIG. 11 a perspective view of a data connector of the equipment support and a complementary data connector of a hospital bed or a support arm;

DESCRIPTION OF THE ILLUSTRATIVE EMBODIMENTS

Figure 2:
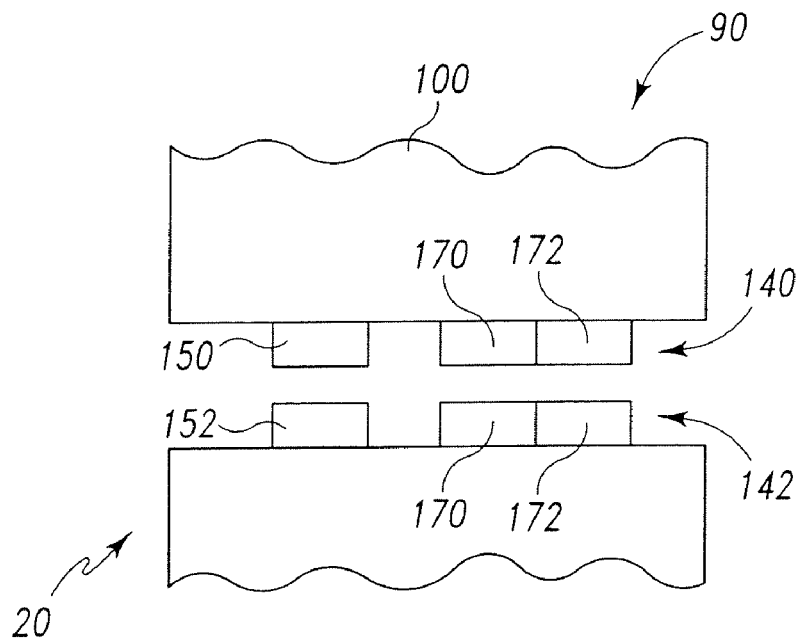
FIG. 2 is a diagrammatic view of couplers between the equipment support and the support arm.
Figure 3:
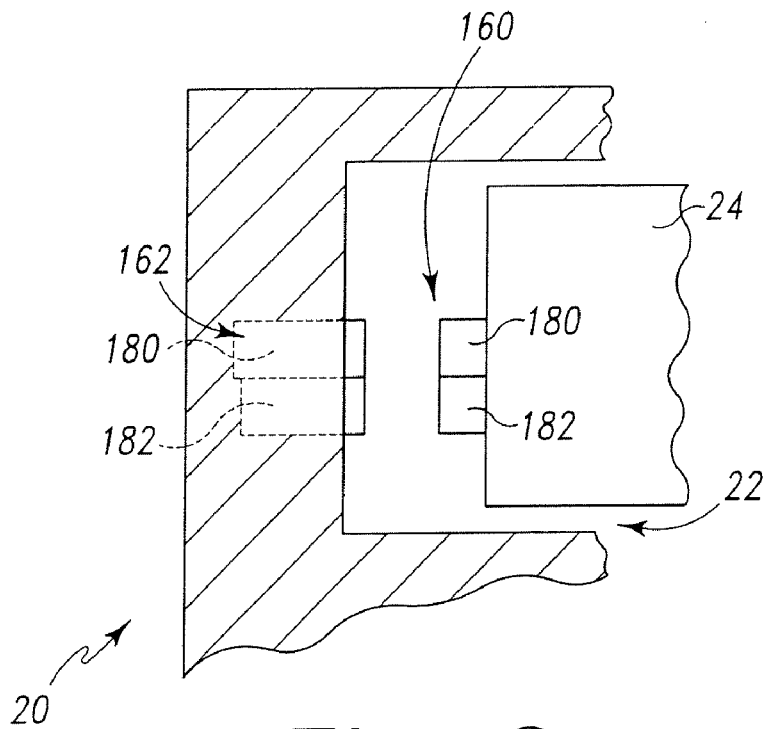
FIG. 3 is a diagrammatic view of couplers between the equipment support and a patient care module.
Figure 4:
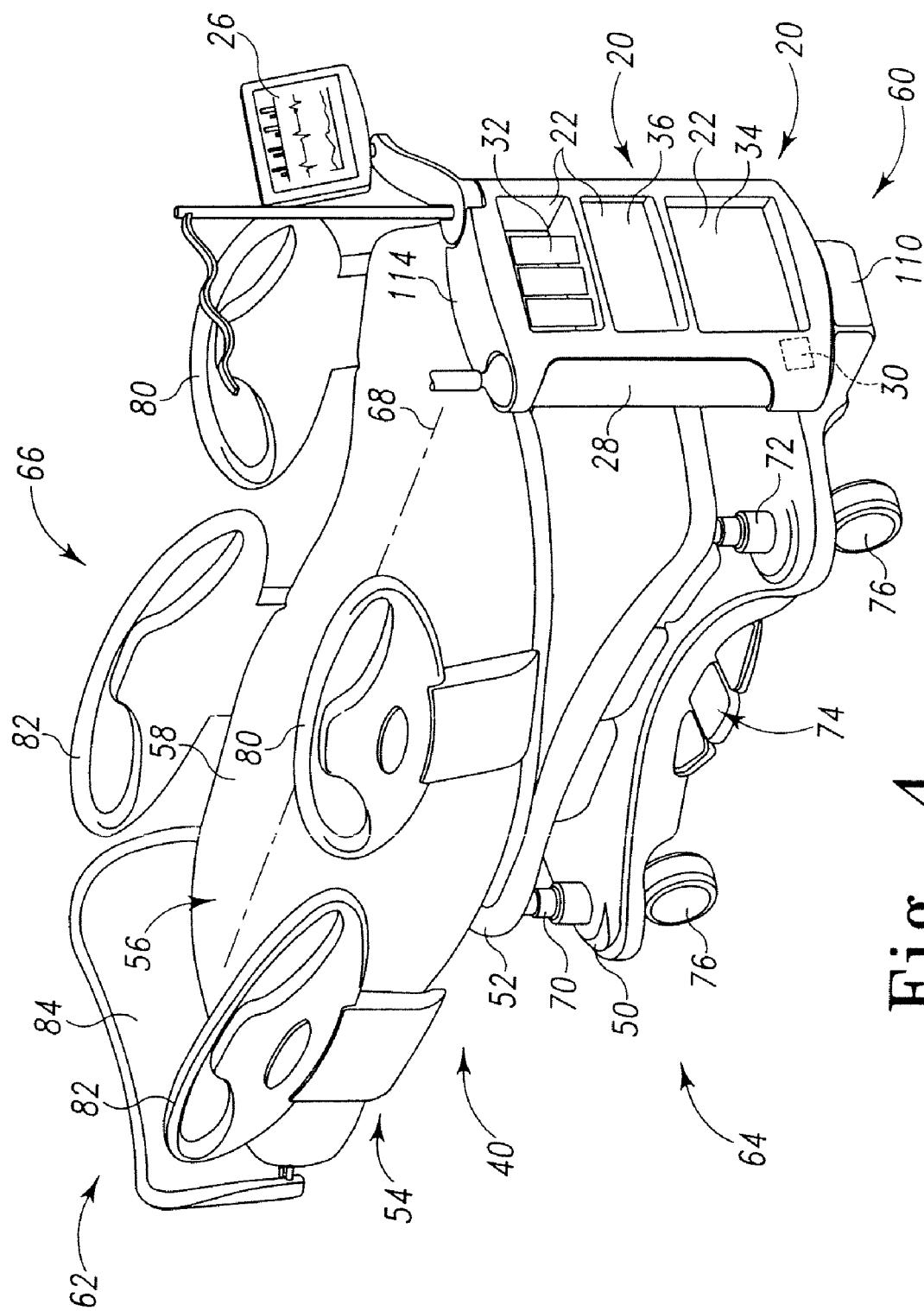
FIG. 4 is a perspective view of the equipment support coupled to a hospital bed showing the patient care modules received in the respective equipment-receiving cavities in the equipment support.

Referring to FIGS. 1-5, a patient care equipment support 20 has a plurality of equipment-receiving cavities 22 configured for receiving patient care equipment or modules 24. Examples of modules 24 that may be received in the equipment-receiving cavities 22 include: an infusion pump, a ventilator, a cardiac monitor, a pulse oximeter, a non-invasive blood pressure measuring device, a digital thermometer, a liquid oxygen module, a defibrillator, a respiratory rate measuring device, medical gas delivery equipment (such as an oxygen tank), intra-venous bags, and the like. Many patient care modules 24 connect via lines or tubes to a patient (not shown) supported on a hospital bed 40. As shown in FIG. 4, patient data received by one or more of the patient care modules 24 is displayed on a display screen 26 of a user interface device attached to the equipment support 20. In the illustrated embodiment, the display screen 26 is a flat panel touchscreen display. Some examples of patient data are blood pressure, temperature, pulse rate, respiratory rate, blood oxygen saturation level, patient weight, and the like. The equipment support 20 is configured to carry an oxygen tank 28 as shown in FIG. 4. Furthermore, equipment support 20 has a microcontroller 30, shown in phantom in FIG. 4, that is coupled to modules 24 and to display 26.

Figure 1:
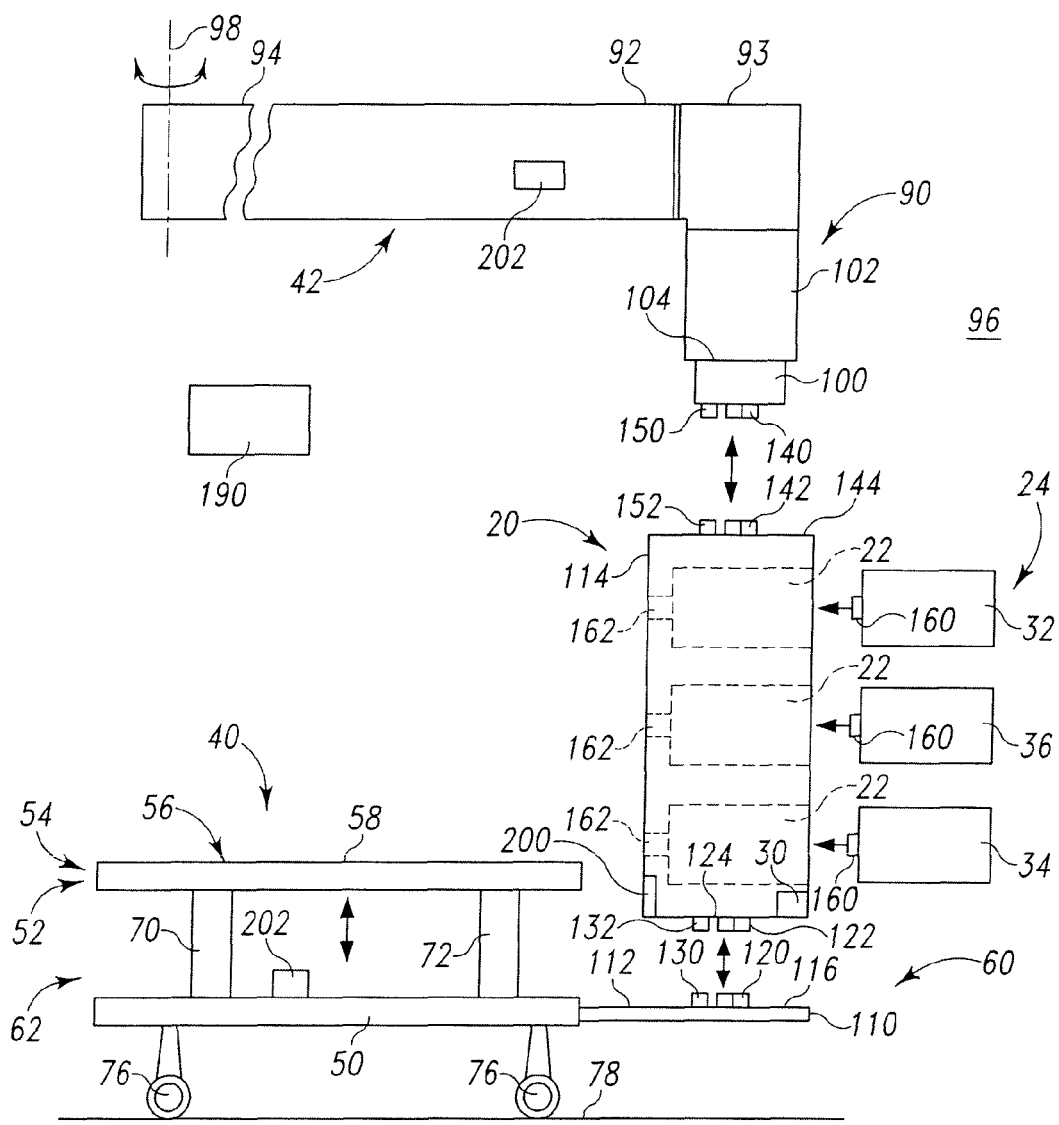
FIG. 1 is a diagrammatic view of a patient care equipment support transferable between a hospital bed and an overhead support arm.
Figure 5:
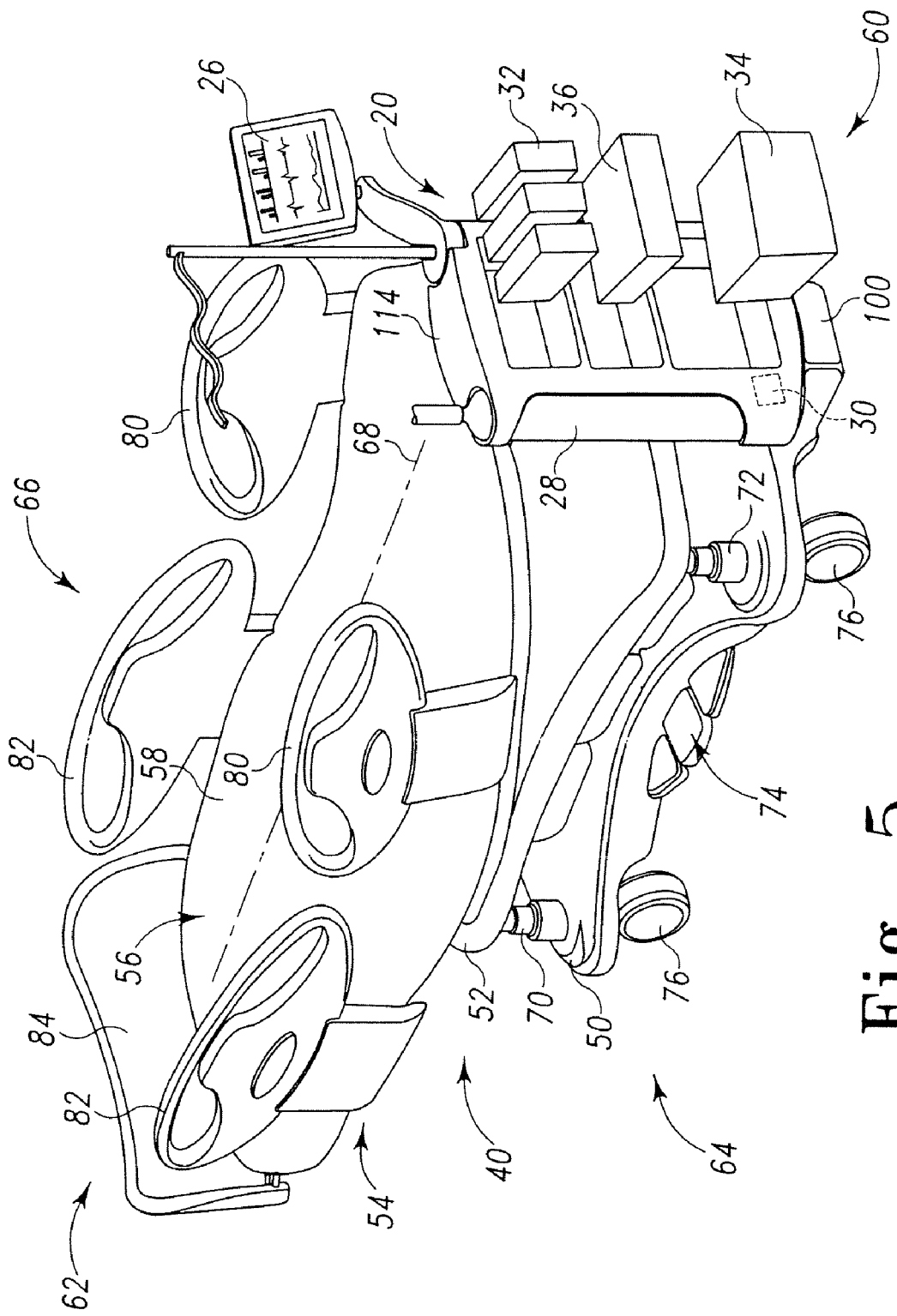
FIG. 5 is a perspective view similar to FIG. 4 of the equipment support coupled to the hospital bed showing the patient care modules withdrawn from the respective cavities in the equipment support.

The equipment support 20 illustrated in FIGS. 1, 4 and 5 has three cavities 22, one each for a set of infusion pumps 32, a ventilator 34, and a patient monitor 36. One cavity 22 is shaped and sized for receiving four infusion pumps 32 arranged side by side therein. Two cavities 22 are shaped and sized for receiving the ventilator 34 and the patient monitor 36, respectively. The actual number of equipment-receiving cavities 22 depends on design considerations. Although the illustrated equipment support 20 has three cavities 22, the equipment support 20 may very well have more or less than three cavities 22. Illustratively, the equipment support 20 is in the form of a rectangular, box-shaped structure with the cavities 22 provided therein. However, the equipment support 20 may have any desired shape and, in some cases, the equipment support 20 may be in the form of a spine or a column (not shown) with pre-assigned spaces for the associated patient care modules 24.

The equipment support 20 is adapted to be transferable between a first device, such as the hospital bed 40, and a second device, such as an overhead support arm 42. As shown in FIGS. 4 and 5, the bed 40 includes a base frame 50, an upper frame 52 supported above the base frame 50, and an articulating deck 54 supported above the upper frame 52. A mattress 56 having a patient support surface 58 rests on the deck 54. The bed 40 includes a head end 60, a foot end 62, a first side 64, a second side 66, and a longitudinal axis 68. A set of jacks 70, 72 are interposed between the base frame 50 and the underside of the upper frame 52. A plurality of foot pedals 74 are coupled to the base frame 50 to operate the jacks 70, 72 to raise and lower the upper frame 52.

The deck 54 has longitudinally-spaced head, seat, thigh and foot sections. The seat section is fixed to the upper frame 52, and the head, thigh and foot sections are movable relative to each other and relative to the seat section. The base frame 50 is supported on four wheels 76. The outer periphery of the upper frame 52 defines a footprint when projected downwardly onto a floor 78. Two side rails 80 are coupled to the head section of the deck 54. Two side rails 82 are coupled to the upper frame 52 or to the foot section of the deck 54. A foot board 84 is coupled to the foot end 62 of the upper frame 52.

As shown in FIG. 1, a telescopic column 90 is coupled to a distal end 92 of the support arm 42 by a coupler 93. A proximal end 94 of the support arm 42 is supported by a ceiling or a wall of a hospital room 96. Alternatively, the proximal end 94 of the support arm 42 is supported by a support structure that extends upwardly from the floor 78 of the hospital room 96. The support arm 42 is pivotable about a substantially vertical axis 98 extending through the proximal end 94. In the illustrative embodiment, the support arm 42 is telescopic so that its distal end 92 telescopes horizontally relative to its proximal end 94. Non-telescopic arms are contemplated by this disclosure as well.

The telescopic column 90 has a lower portion 100 that telescopes vertically relative to an upper portion 102 under the power of an electric motor or other suitable driver housed in the upper portion 102. Illustratively, the motor is a linear actuator of the type commercially available from the Linak Company of Denmark. It is understood that drivers such as hydraulic cylinders, magnetic cylinders, pneumatic cylinders, and the like may be used in lieu of the motor to cause the vertical telescopic movement of the lower portion 100 of the column 90. The motor is actuated by a user control (not shown) positioned on the telescopic column 90 or a wall of the hospital room 96. Alternatively, the motor may be operated by a wired or wireless remote control.

The vertical telescoping movement of the column 90 permits the equipment support 20 to be lifted off the bed 40 and attached to the column 90. Additionally, such vertical telescoping movement of the column 90 permits the equipment support 20 to be detached from the column 90 and reattached to the bed 40. The pivoting movement of the support arm 42 about the vertical axis 98, the horizontal telescoping movement of the support arm 42, and the vertical telescoping movement of the column 90 allow the equipment support 20 to be positioned at any desirable location within a range of movements.

The bed 40, the support arm 42, and the column 90 merely illustrate the environment for the operation of the equipment support 20. It will be understood that the first device may very well be any one of the following: a stretcher, a surgery table, an ambulatory care chair, a wheeled carriage, a patient support, and the like. Likewise, the second device may very well be any one of the following: a cart, a stand, an arm, and the like.

Figure 15:
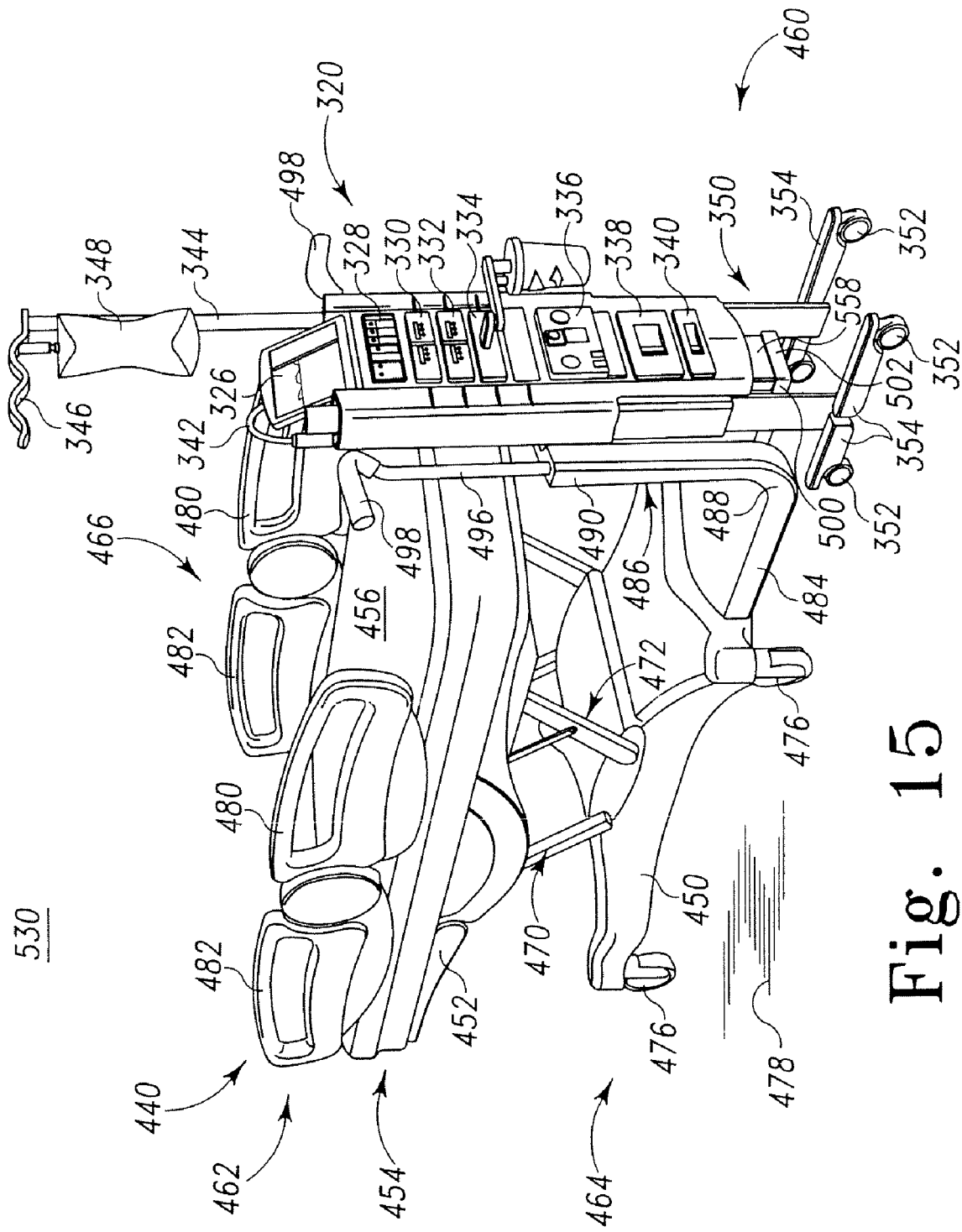
FIG. 15 is a perspective view, similar to FIG. 14, showing the main structure of the equipment support moved downwardly by a sufficient amount so that a coupler of the equipment support mates with a coupler carried by the support ledge.
Figure 16:
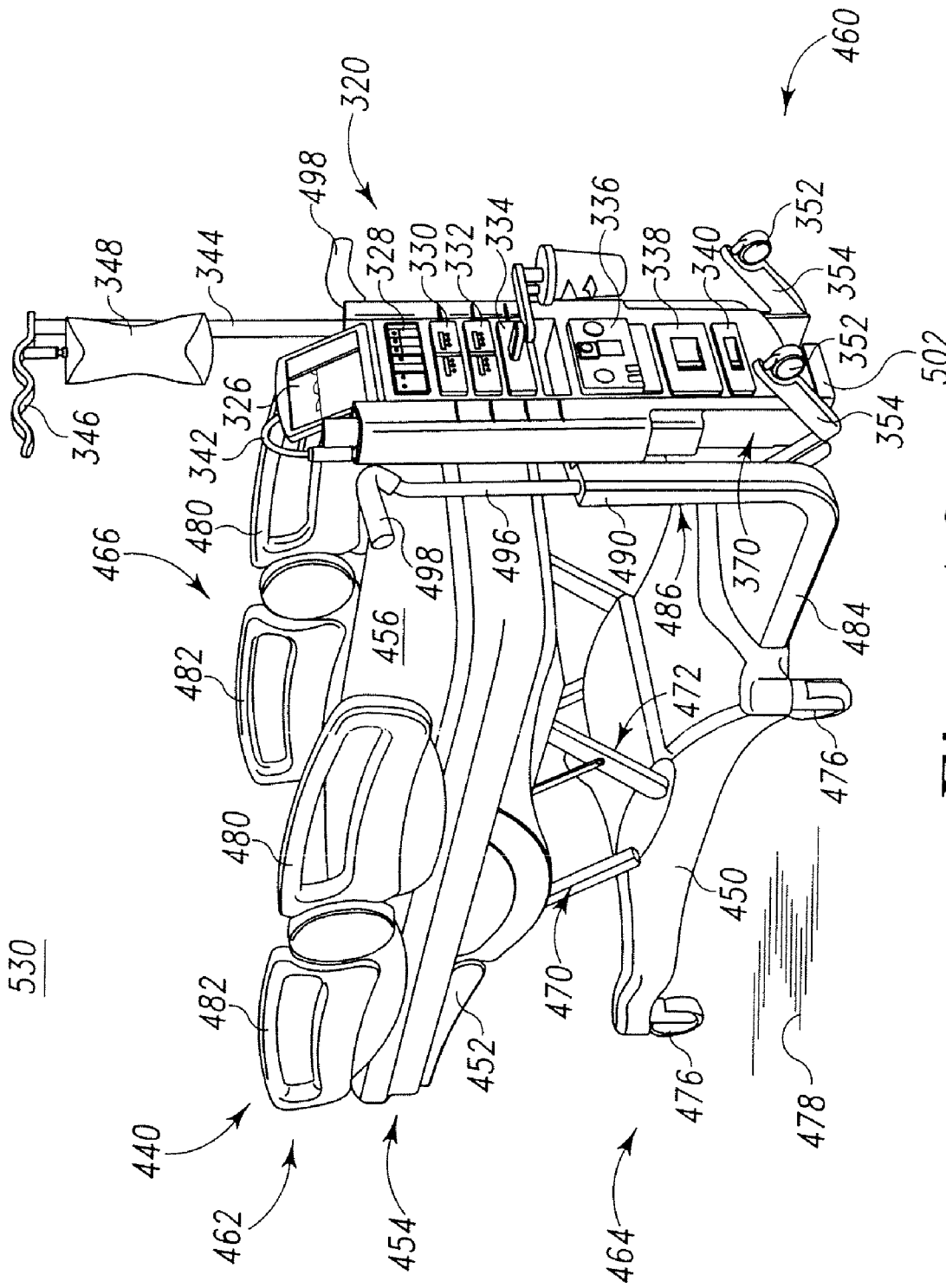
FIG. 16 is a perspective view, similar to FIG. 15, showing vertically extending first members of the support legs retracted upwardly relative to the main structure of the equipment support and pairs of pivotable second members to which wheels are coupled pivoted upwardly to respective intermediate positions.
Figure 17:
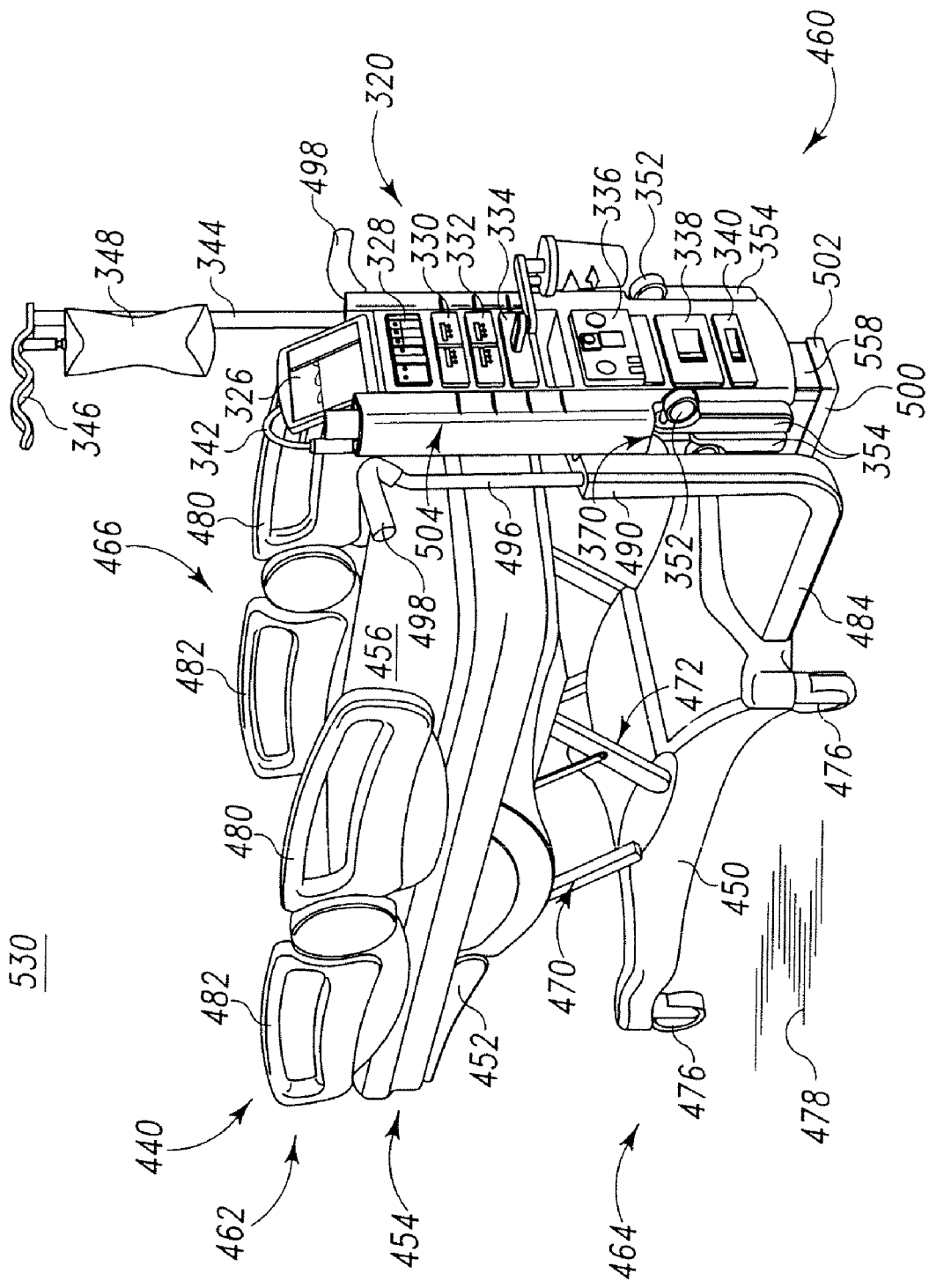
FIG. 17 is a perspective view, similar to FIG. 16, showing the first members further retracted upwardly relative to the main structure of the equipment support and showing the second members pivoted to storage positions alongside the first members.
Figure 18:
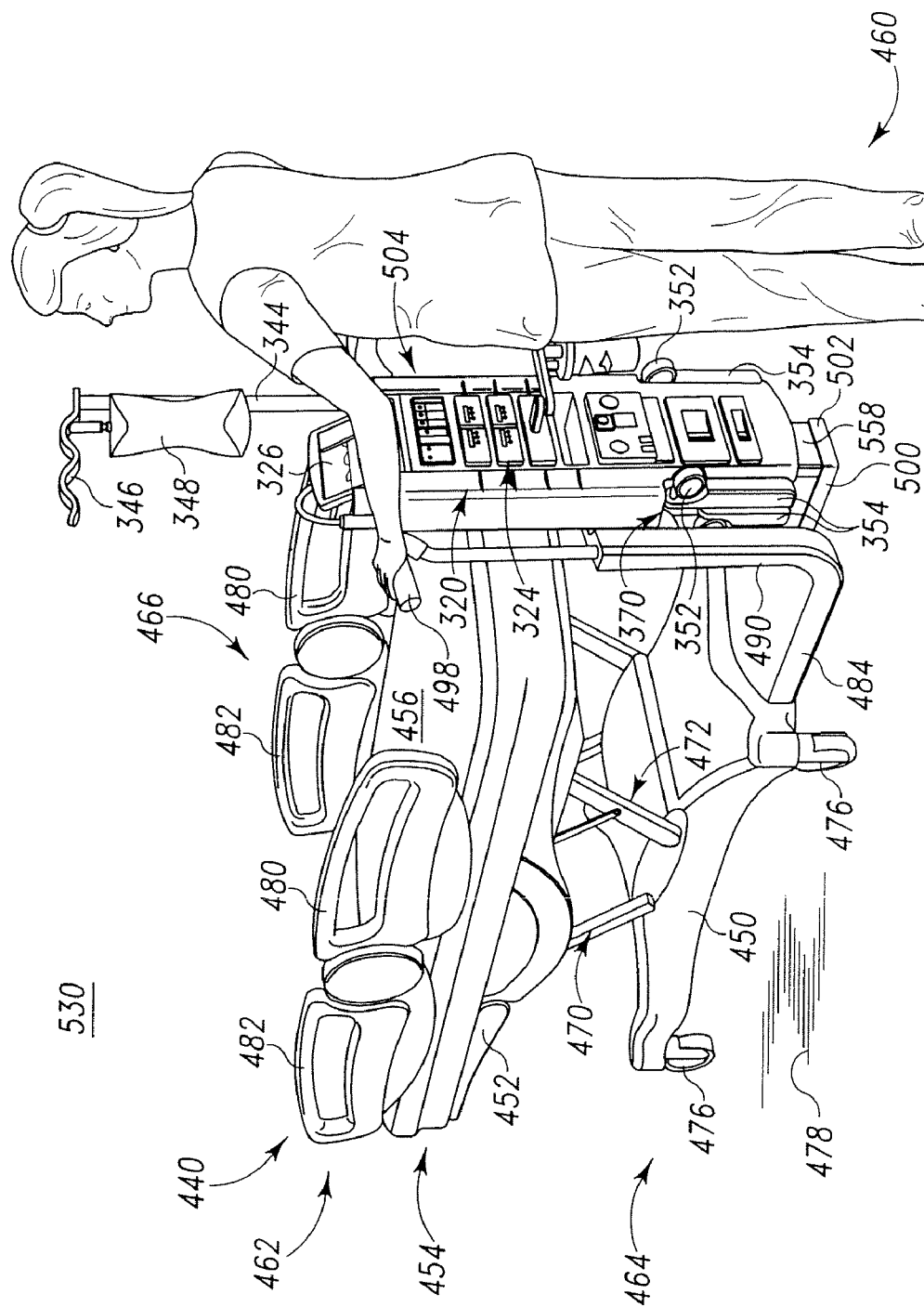
FIG. 18 is a perspective view, similar to FIG. 17, showing a caregiver grasping push handles of the hospital bed situated on either side of the equipment support which is being carried by the hospital bed.
Figure 19:
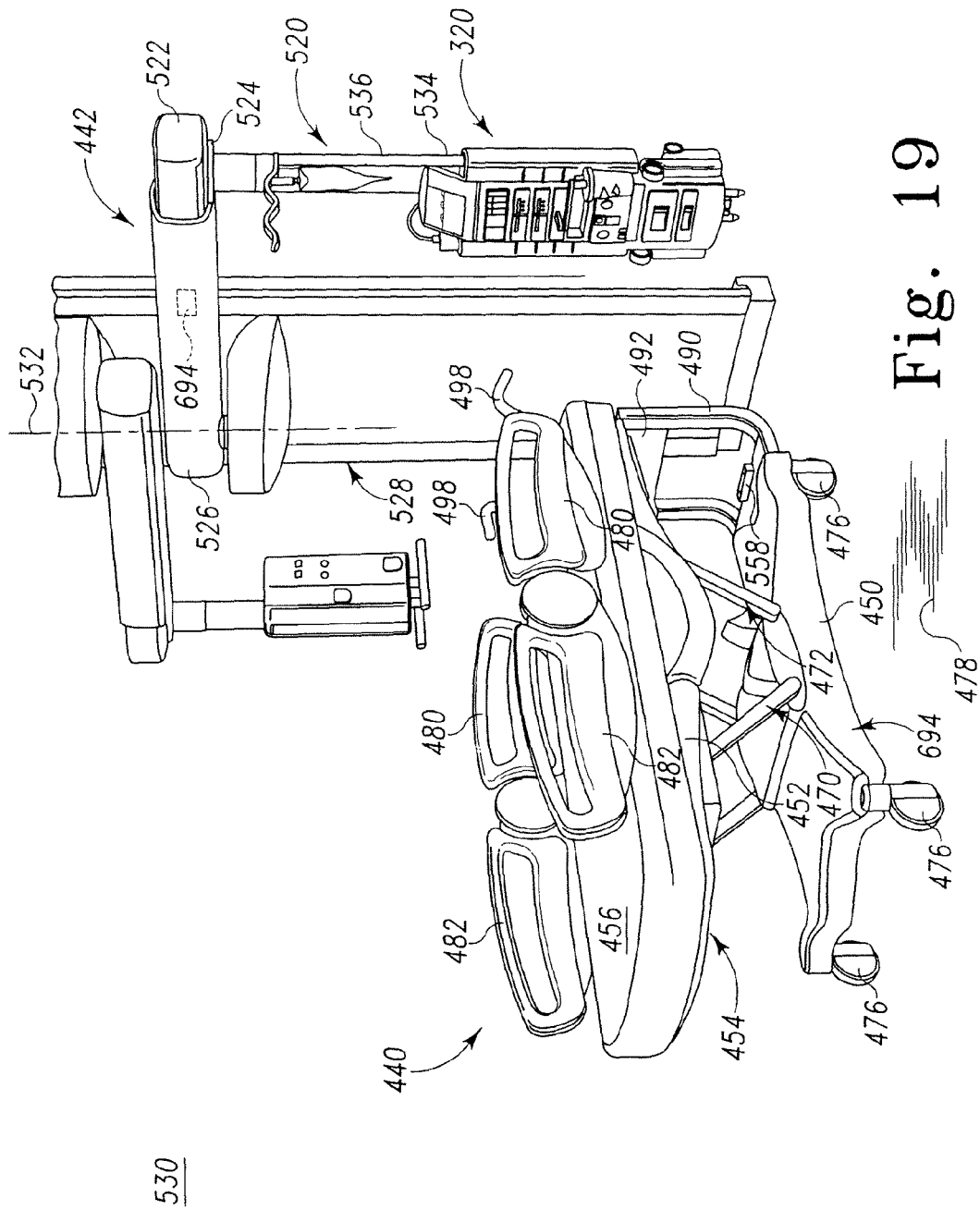
FIG. 19 is a perspective view showing the equipment support transferred from the hospital bed onto a support arm which suspends the equipment support above a floor of the hospital room.

In some embodiments, the equipment support 20 includes extendible support legs with floor-engaging wheels (such as the extendible support legs 350 with floor-engaging wheels 352 shown in FIGS. 6, 8, 9 and 12-19) which allow the equipment support 20 to be decoupled from the bed 40 or the column 90 and supported on the floor 78 for independent operation thereof. The support legs are configured to retract when the equipment support 20 is lifted off the floor 78 and attached to the bed 40 or the column 90 as shown in FIGS. 17-19.

As shown in FIG. 1, a support structure or ledge 110 extends outwardly from the head end 60 the base frame 50. Illustratively, the ledge 110 is spaced from the floor 78. At least a portion 112 of the ledge 110 extends outside the footprint of the upper frame 52. The equipment support 20 is detachably coupled to the ledge 110 outside the footprint of the upper frame 52. The width of the equipment support 20 is less than the width of the base frame 50. The width of the ledge 110 is less than the width of the equipment support 20. In some embodiments, the width of the equipment support 20 is equal to the width of the base frame 50. In some embodiments, the width of the ledge 110 is equal to the width of the equipment support 20.

When the equipment support 20 is coupled to structure 110 of the base frame 50, an upper portion 114 of the equipment support 20 is situated above the upper frame 52. Attachment of the equipment support 20 to the base frame 50, instead of the upper frame 52, allows the equipment support 20 to be taller than some prior art equipment supports which enables it to have an increased number of equipment-receiving cavities 22 for receiving multiple patient care modules 24.

The top 116 of the ledge 110 of the bed 40 has first power and data connectors 120 and a first mechanical connector 130. The bottom 104 of the lower portion 100 of the support column 90 has second power and data connectors 140 and a second mechanical connector 150. The equipment support 20 has third power and data connectors 122 and a third mechanical connector 132 coupled to the underside 124 of the equipment support 20. The equipment support 20 has fourth power and data connectors 142 and a fourth mechanical connector 152 coupled to the topside 144 of the equipment support 20.

The equipment support 20 is configured to be detachably coupled to the bed 40. As the equipment support 20 approaches the bed 40, the third mechanical connector 132 engages the first mechanical connector 130 before the third power and data connectors 122 engage the first power and data connectors 120 to align the third power and data connectors 122 with the first power and data connectors 120. As the engagement between the third mechanical connector 132 and the first mechanical connector 130 progresses, the third power and data connectors 122 couple to the first power and data connectors 120 to supply power to the equipment support 20 and to establish a communication link between the equipment support 20 and the bed 40. The engagement between the third mechanical connector 132 and the first mechanical connector 130 secures the equipment support 20 to the bed 40.

The equipment support 20 is configured to be detachably coupled to the column 90. As the column 90 approaches the equipment support 20, the second mechanical connector 150 engages the fourth mechanical connector 152 before the second power and data connectors 140 engage the fourth power and data connectors 142 to align the second power and data connectors 140 with the fourth power and data connectors 142. As the engagement between the second mechanical connector 150 and the fourth mechanical connector 152 progresses, the second power and data connectors 140 couple to the fourth power and data connectors 142 to supply power to the equipment support 20 and to establish a communication link between the equipment support 20 and the column 90. The engagement between the second mechanical connector 150 and the fourth mechanical connector 152 secures the equipment support 20 to the column 90.

The third and the fourth power and data connectors 122, 142 are arranged on the equipment support 20 so that the first and second power and data connectors 120, 140 can be coupled substantially simultaneously to the respective third and fourth power and data connectors 122, 142 before disconnection of either one of the first and second power and data connectors 120, 140 from the respective third and fourth power and data connectors 122, 142 to permit the equipment support 20 to be transferred between the bed 40 and the column 90 without a loss of power to the equipment support 20 or without a loss of communication link with the equipment support 20.

Likewise, the third and fourth mechanical connectors 132, 152 are arranged on the equipment support 20 so that the first and second mechanical connectors 130, 150 can be coupled substantially simultaneously to the respective third and fourth mechanical connectors 132, 152 before disconnection of either one of the first and second mechanical connectors 130, 150 from the respective third and fourth mechanical connectors 132, 152. This assures that the equipment support 20 is firmly secured to the bed 40 before it is released from the column 90, and firmly secured to the column 90 before it is released from the bed 40.

Each patient care module 24 has power and data connectors 160 which are configured to be coupled to associated power and data connectors 162 of the equipment support 20 to supply power to the patient care module 24 and to establish a communication link between the patient care module 24 and the equipment support 20 when the patient care module 24 is received in the associated equipment-receiving cavity 22 in the equipment support 20. Thus, each of the infusion pump 32, the ventilator 34 and the patient monitor 36 has power and data connectors 160 which are configured to be coupled to associated power and data connectors 162 of the equipment support 20. The power and data connectors 162 of the equipment support 20 are accessible for connection to the power and data connectors 160 of the patient care module 24 through respective openings (not shown) in an interior wall of the equipment support 20.

FIG. 2 is a schematic representation of the second and fourth power and data connectors 140, 142 and the second and fourth mechanical connectors 150, 152. The first and third power and data connectors 120, 122 are similar to the second and fourth power and data connectors 140, 142, and the first and third mechanical connectors 130, 132 are similar to the second and fourth mechanical connectors 150, 152. The second and fourth mechanical connectors 150, 152 serve to align the second and fourth power and data connectors 140 and to secure the equipment support 20 to the column 90. Likewise, the first and third mechanical connectors 130, 132 serve to align the first and third power and data connectors 120, 122 and to secure the equipment support 20 to the bed 40. FIG. 3 is a schematic representation of the power and data connectors 160, 162.

Locating pins (such as the pins 550, 572 shown in FIGS. 9 and 12) sized for cooperative mating engagement with associated sockets (such as the sockets 554, 578 shown in FIGS. 14 and 20) may be used for aligning the equipment support 20 with the bed 40 and the column 90. Latches (not shown) may be used for locking the equipment support 20 to the bed 40 or the column 90, as the case may be. Illustrative locating pins, sockets and latches are disclosed in 1) U.S. Pat. App. Pub. No. US2005/0000019, entitled "Patient Care Equipment Management System," 2) PCT Pat. App. Pub. No. WO2005/037165, entitled "Patient Care Equipment Support Lock," and 3) U.S. Pat. No. 4,795,122, all of which are hereby incorporated by reference herein.

In some embodiments, each one of first, second, third and fourth power and data connectors 120, 140, 122, 142 includes a first wired power coupler 170 to supply electrical power to the equipment support 20 and a second wireless data coupler 172 to establish a communication link between the equipment support 20 and the bed 40 or the support column 90, as the case may be. Each one of power and data connectors 160, 162 includes a first wired power coupler 180 to supply electrical power to the patient care module 24 and a second wireless data coupler 182 to establish a communication link between the patient care module 24 and the equipment support 20.

The wired couplers 170, 180 comprise electrical contacts. The wireless couplers 172, 182 comprise one or more of the following: a photoemitter, a photodetector, a photodiode, a radio frequency (RF) transmitter, an RF receiver, an RF transceiver, an infrared (IR) transmitter, an IR receiver, and an IR transceiver. Alternatively, wired data couplers may be used in lieu of the wireless data couplers 172, 182. Data from the patient care module 24 is wirelessly communicated to a computer network 190 of a healthcare system so that other computer devices connected to the computer network 190 have access to the data from the patient care module 24 when the patient care module 24 is received in the associated equipment-receiving cavity 22 in the equipment support 20 and the equipment support 20 is coupled to the bed 40 or the column 90.

The wireless communication between the patient care module 24 and the computer network 190 may be in accordance with any desired protocol, including the following protocols: IrDA, spread spectrum (including the Bluetooth protocol), RS232, TCP/IP, USB, and 802.11$_x$. The wireless communication may use frequency modulation or by frequency modulated infrared (FMIR). In some embodiments, data includes control signals for the operation of the patient care modules 24, the display 26 or the microcontroller 30. The power and data connectors 120, 122, 140, 142, 160, 162 may be of the type illustrated in PCT Pat. App. Pub. No. WO2005/022692, entitled "Plug and Receptacle Having Wired and Wireless Coupling."

In some embodiments, the power and data connectors 160, 162 of the patient care module 24 and the equipment support 20 are drawer connectors to facilitate blind mating when the patient care module 24 is inserted into the associated equipment-receiving cavity 22 of the equipment support 20. Such drawer connectors may be of the type illustrated in U.S. Pat. No. 4,664,456. In some embodiments, the power and data connector 162 of the equipment support 20 is a receptacle connector and the power and data connector 160 of the patient care module 24 is a plug connector.

Figure 22:
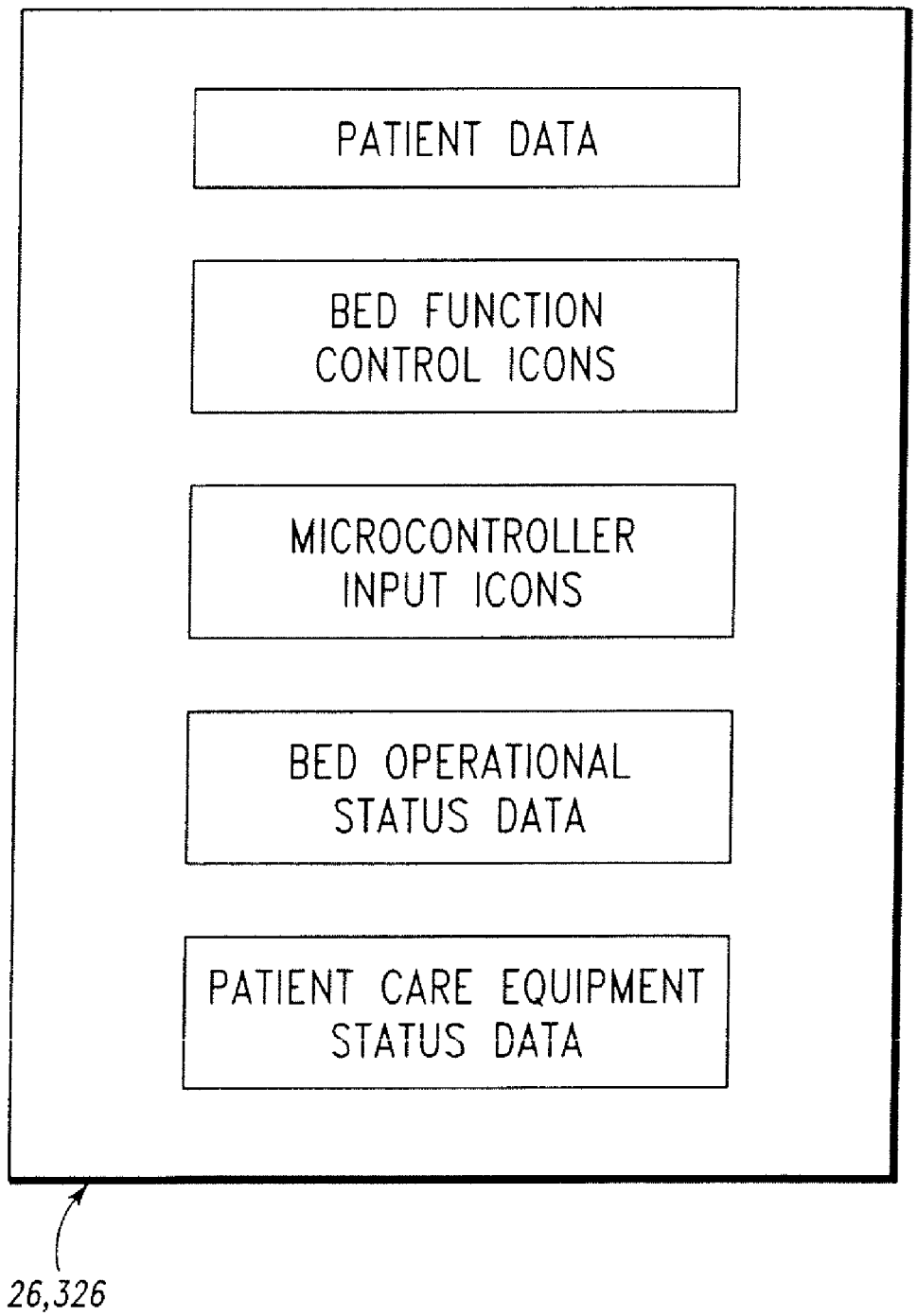
FIG. 22 is a screen shot of a display screen showing patient data, bed function control icons, microcontroller input icons, bed operational status data, and patient care equipment status data.

As shown in FIG. 22, the display 26 is operable in several modes, either at the same time or at different times, when the equipment support 20 is coupled to the bed 40. In a first mode, the display 26 is operable to display patient data. Illustratively, the patient data includes blood pressure, temperature, pulse rate, respiratory rate, blood oxygen saturation level, patient weight, and the like. This list is intended to be exemplary, not exhaustive, and it is contemplated by this disclosure that all types of patient data may be displayed on the display 26. In a second mode, the display 26 is operable to display a first plurality of icons that are touchable to move the movable portions of the bed 40, such as the head, thigh and foot sections of the deck 54 and the side rails 80, 82. Thus, display 26 is a touchscreen display in some embodiments. In a third mode, the display 26 is operable to display a second plurality of icons that are touchable to provide input to the microcontroller 30. In a fourth mode, the display 26 is configured to display the operational status of the bed 40 including one or more of the following: bed function lock-outs, bed articulation, bed elevation, siderail positions, and therapy surface data. In a fifth mode, the display 26 is configured to display the operational status of the patient care modules 24 including information concerning one or more of the following: alarm status and the equipment settings.

The equipment support 20 has an on-board battery 200 for supplying power to the patient care modules 24, the display 26 and the microcontroller 30. Alternatively, the bed 40 and the support arm 42 each has a power source, such as, for example, a battery 202 or a converter to convert a line voltage to a low DC voltage, for supplying power to the patient care modules 24, the display 26 and the microcontroller 30 when the equipment support 20 is coupled to the bed 40 or the support arm 42. The equipment support 20 has conductors for electrically coupling the patient care modules 24, the display 26 and the microcontroller 30 to the power and data connectors 122, 142. Conductors may also extend between the display 26, the microcontroller 30 and the power and data connectors 162.

FIGS. 6-20 show another embodiment of a patient care equipment support 320. Portions of the equipment support 320 are substantially the same or similar as the like portions of the equipment support 20. The equipment support 320 has a plurality of equipment-receiving cavities 322 configured for receiving patient care modules 324. Many patient care modules 324 connect via lines or tubes to a patient (not shown) supported on a hospital bed 440. Patient data received by the patient care modules 324 is displayed on a display screen 326 of a user interface device attached to the equipment support 320. In the illustrated embodiment, the display screen 326 is a flat panel touchscreen display. The equipment support 320 includes an on-board microcontroller 692 (FIG. 8) coupled to the display 326.

Figure 6:
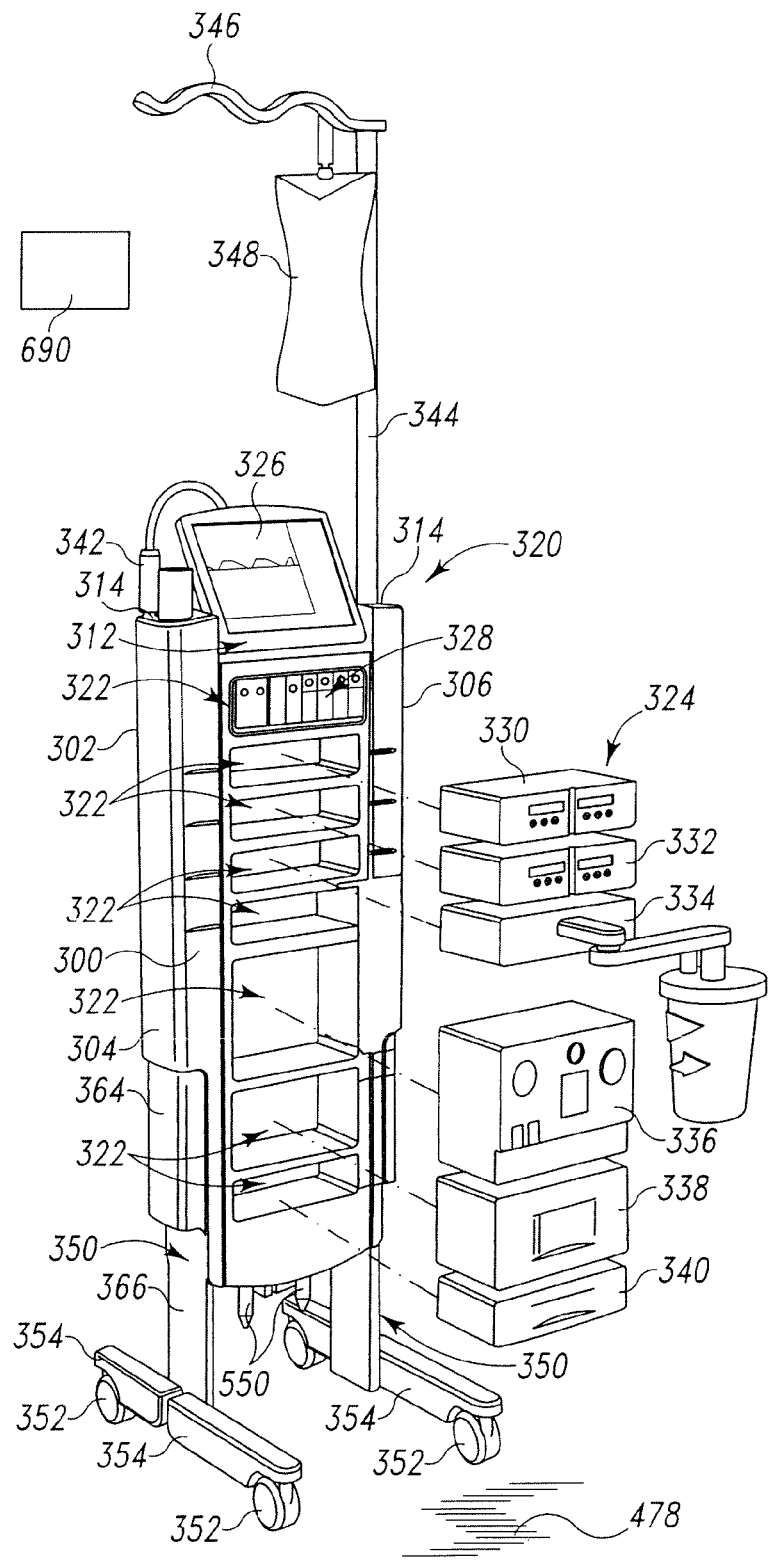
FIG. 6 is a perspective view of a second embodiment of the patient care equipment support having a main structure and a pair of extendible support legs extending downwardly from the main structure.
Figure 8:
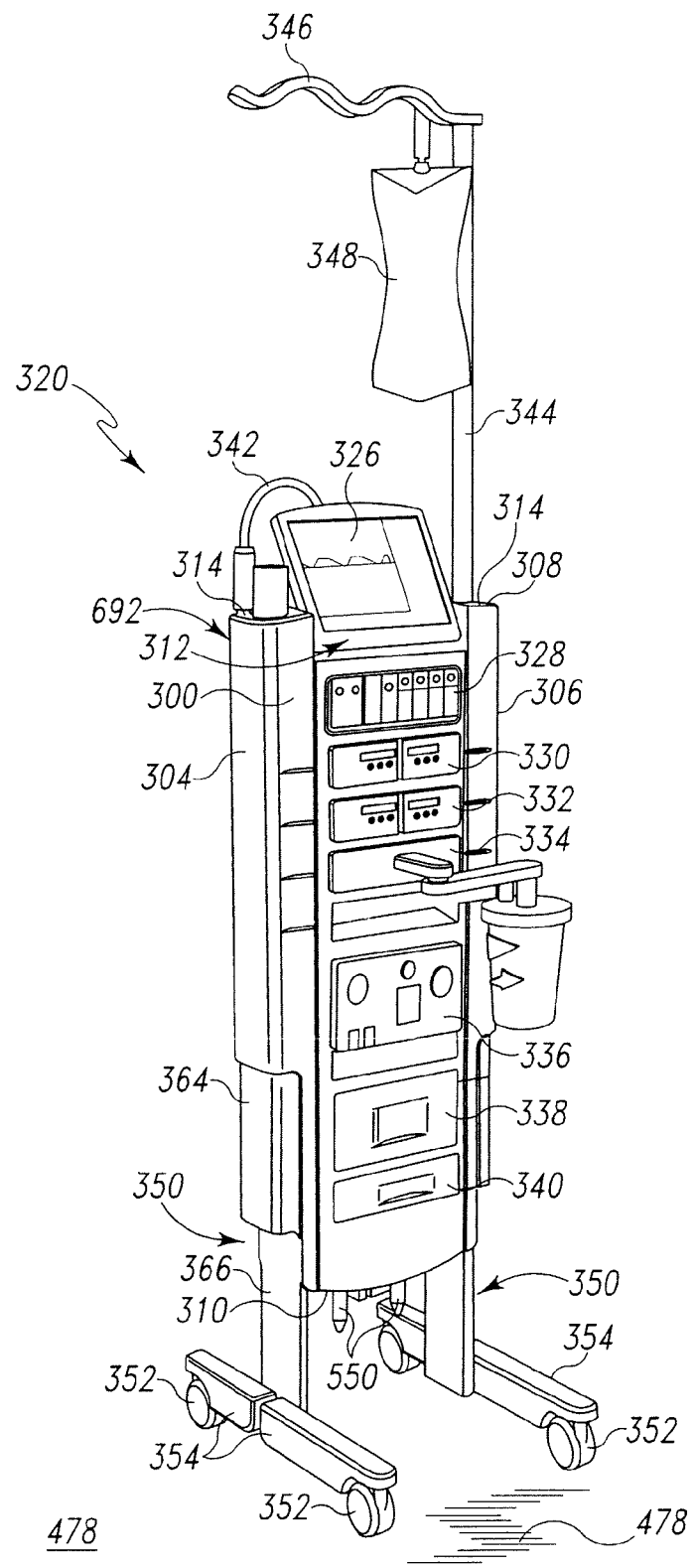
FIG. 8 is a perspective view of the equipment support showing the patient care modules received in the associated equipment-receiving cavities in the equipment support.

As shown, for example, in FIGS. 6, 8, 9 and 12, the equipment support 320 is in the form of a rectangular, box-shaped main structure having a front wall 300, a back wall 302, a pair of side walls 304, 306, a top wall 308 and a bottom wall 310. In the illustrated embodiment, the equipment support 320 has eight cavities 322 that are accessible from the front wall 300 of the equipment support 320. As shown in FIGS. 6 and 8, seven of the eight cavities 322 are allocated to various module 324 and one cavity 322 is unallocated. Each cavity 322 is shaped and sized to receive one or more specific modules 324. In the illustrated embodiment, seven of the eight cavities 322 are allocated as follows: 1) a plurality of mini modules 328 (such as pulse oximeter, non-invasive blood pressure measuring module, and the like), 2) a first dual channel IV pump module 330, 3) a second dual channel IV pump module 332, 4) a portable suction module 334, 5) a ventilator module 336, 6) a liquid oxygen module 338, and 7) a battery module 340. The unallocated cavity 322 may be configured to receive any suitable module 324, such as, for example, a cardiac monitor, an apnea monitor, a respiratory rate measuring module, and the like.

As shown, for example, in FIGS. 6 and 8, the top wall 308 of the equipment support 320 comprises a central recess 312 disposed between two raised shelf portions 314. A digital thermometer 342 is coupled to one of the two shelf portions 314 near the left side wall 304. An IV pole 344 is coupled to the other of the two shelf portions 314 near the right side wall 306. The IV pole 344 has a cantilevered arm 346 for supporting one or more IV bags 348.

Although the illustrated equipment support 320 has eight cavities 322, the equipment support 320 may very well have more or less than eight cavities 322. Likewise, although a specific allocation of the eight cavities 322 is made in the illustrated embodiment, a different allocation of the eight cavities 322 may very well be made. Although the illustrated equipment support 320 has a rectangular, box-shaped main structure, it may very well have a main structure of any desired shape. In some cases, the main structure of the equipment support 320 may be in the form of a spine or a column (not shown) with pre-assigned spaces for specific patient care modules 24.

As shown in FIG. 19, the equipment support 320 is adapted to be transferable between a first device, such as the hospital bed 440, and a second device, such as an overhead support arm 442. In the illustrated example, the bed 440 and the support arm 442 merely illustrate the environment for the operation of the equipment support 320. It will be understood that the first device may very well be any one of the following: a stretcher, a surgery table, an ambulatory care chair, a wheeled carriage, a patient support, and the like. Likewise, the second device may very well be any one of the following: a cart, a stand, an arm, and the like.

Figure 12:
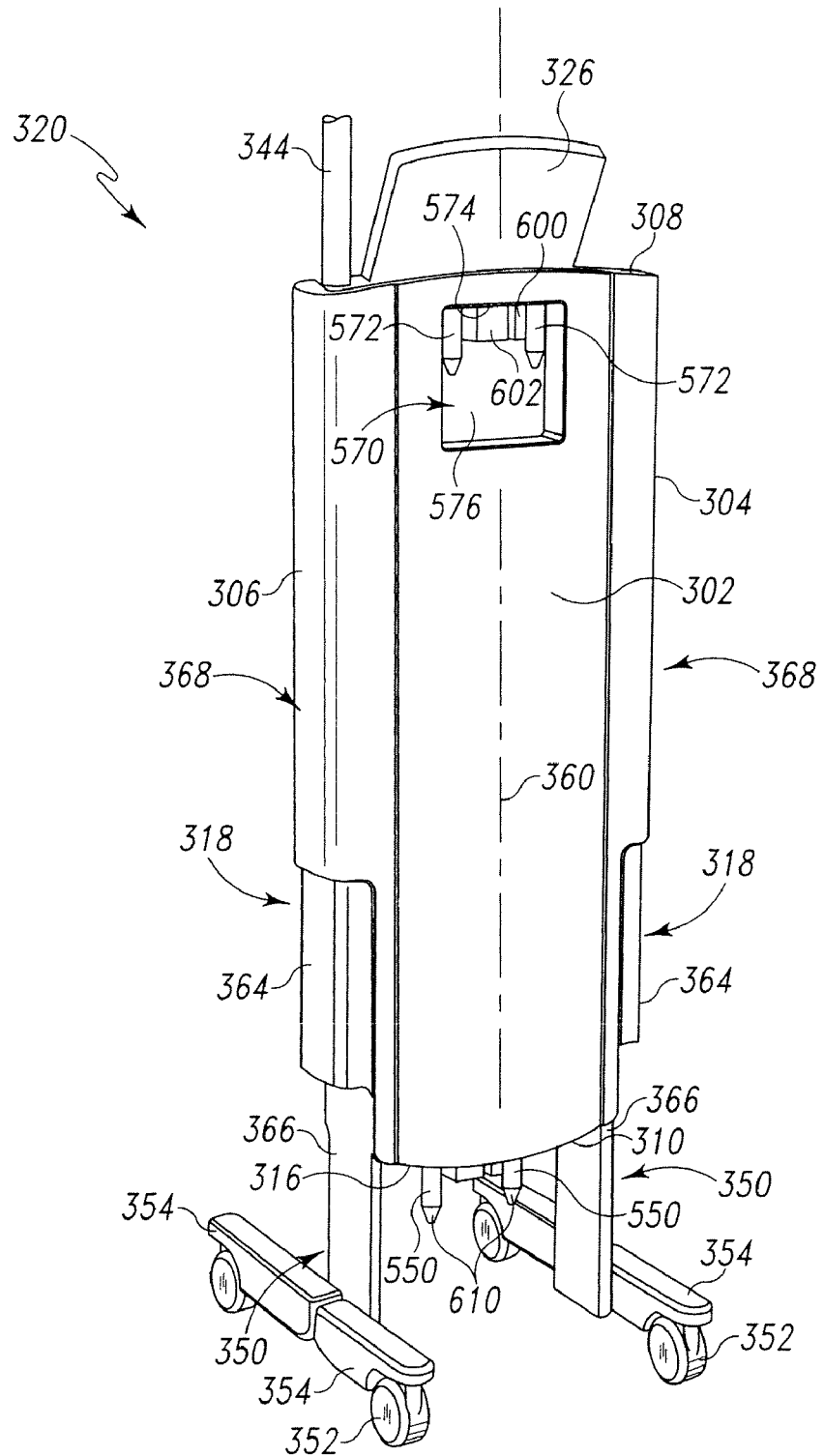
FIG. 12 is a perspective view of the equipment support showing a pair of coupling pins, a power connector and a data connector extending downwardly from a downwardly-facing wall of a cavity formed in a back wall of the equipment support.

As shown, for example, in FIGS. 6, 8, 9 and 12, the equipment support 320 includes a pair of downwardly-extending support legs 350 with floor-engaging wheels 352 which allow the equipment support 320 to be decoupled from the bed 440 or the support arm 442 and lowered onto the floor 478 for independent operation thereof. The bottom wall 310 of the equipment support 320 comprises a central downwardly-projecting portion 316 disposed between two vertically-extending recesses 318 as shown in FIGS. 9 and 12. The support legs 350 extend downwardly from respective downwardly-facing surfaces of the recesses 318. The support legs 350 are configured to retract into the associated recesses 318 when the equipment support 320 is lifted off the floor 478 and coupled to the bed 440 as shown in FIGS. 17, 18 or to the support arm 442 as shown in FIG. 19.

Each support leg 350 includes a pair of wheel-supporting members 354. As shown, for example, in FIG. 9, the wheels 352 are coupled to distal ends 356 of the members 354. Proximal ends 358 of the members 354 are coupled to the associated support leg 350 to pivot between an extended position shown in FIGS. 6, 8, 9 and 12-15 where the members 354 extend generally perpendicularly to a longitudinal axis 360 of the equipment support 320 and a retracted position shown in FIGS. 17-19 where the members 354 extend generally parallel to the longitudinal axis 360 of the equipment support 320. As shown in FIGS. 17-19, when retracted, the wheel-supporting members 354 are withdrawn within the respective leg-receiving recesses 318 of the equipment support 320 so that the wheel-supporting members 354 and the associated wheels 352 are within a footprint of the equipment support 320.

The support legs 350 are telescopic. As shown, for example, in FIG. 12, each support leg 350 includes an upper portion 364 and a lower portion 366. Two vertically-extending leg-receiving spaces 368 are formed on the opposite sides 304, 306 of the equipment support 320 above the recesses 318. The upper portions 364 of the support legs 350 retract into the associated leg-receiving spaces 368 shown in FIG. 12 when the support legs 350 are moved to their respective storage positions as shown, for example, in FIGS. 17-19. The upper portions 364 of the support legs 350 extend out of the associated leg-receiving spaces 368 when the support legs 350 are moved to their respective use positions as shown, for example, in FIGS. 6, 8, 9 and 12-15. The lower portions 366 of the support legs 350 are less thick than the respective upper portions 364 (as shown in FIG. 12) to create two opposite wheel-supporting-member-receiving recesses 370 (shown in FIG. 17) into which the pivotable wheel-supporting members 354 are received with their associated wheels 352 as shown in FIG. 17 when the support legs 350 are moved to their respective storage positions.

As the upper portions 364 of the support legs 350 telescope into the respective leg-receiving spaces 368 in the equipment support 320 in the manner shown in FIGS. 15-17, the wheel-supporting members 354 and the associated wheels 352 simultaneously pivot upwardly into their storage positions in the respective wheel-supporting member-receiving recesses 370 formed in the support legs 350. Likewise, as the upper portions 364 of the support legs 350 telescope out the associated leg-receiving spaces 368, the wheel-supporting members 354 and the associated wheels 352 simultaneously pivot downwardly to their respective use positions as shown, for example, in FIGS. 6, 8, 9 and 12-15.

In the illustrated embodiment, one or more electric motors (not shown) housed in equipment support 320 power the telescopic movement of the support legs 350 and the pivoting movement of the wheel-supporting members 354. Each electric motor may be a linear actuator of the type commercially available from the Linak Company of Denmark. It is understood that drivers such as hydraulic cylinders, magnetic cylinders, pneumatic cylinders, and the like may be used in lieu of the electric motors to cause the telescopic movement of the support legs 350 and the pivoting movement of the wheel-supporting members 354. The motors are actuated by associated controls (not shown) positioned on the main structure of the equipment support 320 or by a wired or wireless remote control.

Such vertical telescoping movement of the support legs 350 and the associated pivoting movement of the wheel-supporting members 354 permit the equipment support 320 to be decoupled from the bed 440 or the support arm 442 and supported on the floor 478 as shown in FIGS. 6, 8, 9 and 12-15. Also, such vertical telescoping movement of the support legs 350 and the associated pivoting movement of the wheel-supporting members 354 permit the equipment support 320 to be lifted off the floor 478 and reattached to the bed 440 as shown in FIGS. 16-18, or reattached to the arm 442 as shown in FIG. 19.

As shown in FIGS. 13-19, the bed 440 includes a base frame 450, an upper frame 452 supported above the base frame 450, and an articulating deck 454 supported above the upper frame 452. A mattress 456 having a patient support surface 458 rests on the deck 454. The bed 440 includes a head end 460, a foot end 462, a first side 464, a second side 466, and a longitudinal axis 468. A set of pivotable lift arms 470, 472 are interposed between the base frame 450 and the underside of the upper frame 542. A plurality of foot pedals (not shown) are coupled to the base frame 450 to operate the pivotable lift arms 470, 472 to raise and lower the upper frame 452.

The deck 454 has longitudinally-spaced head, seat, thigh and foot sections. The seat section is fixed to the upper frame 452, and the head, thigh and foot sections are movable relative to each other and relative to the seat section. The base frame 450 is supported on four wheels 476. The outer periphery of the upper frame 452 defines a footprint when projected downwardly onto a floor 478. Two side rails 480 are coupled to the head section of the deck 454. Two side rails 482 are coupled to the upper frame 452 or to the foot section of the deck 754.

As shown in FIGS. 13-19, a first relatively wide ledge 484 extends outwardly in a cantilevered manner from the head end 460 of the base frame 450. The ledge 484 is spaced from the floor 478. In the illustrated example, the width of the ledge 484 is less than the width of the base frame 450. A pair of laterally-spaced frame members 486 shown, for example, in FIG. 13 extend outwardly from the head end 460 of the ledge 484. Each frame member 486 has a first portion 488 that extends horizontally outwardly from the ledge 484 and a second portion 490 that extends vertically upwardly from a distal end of the associated first portion 488. A cross plate 492 extends between the upper regions 494 of the second portions 490 of the frame members 486 as shown, for example, in FIG. 13.

Figure 13:
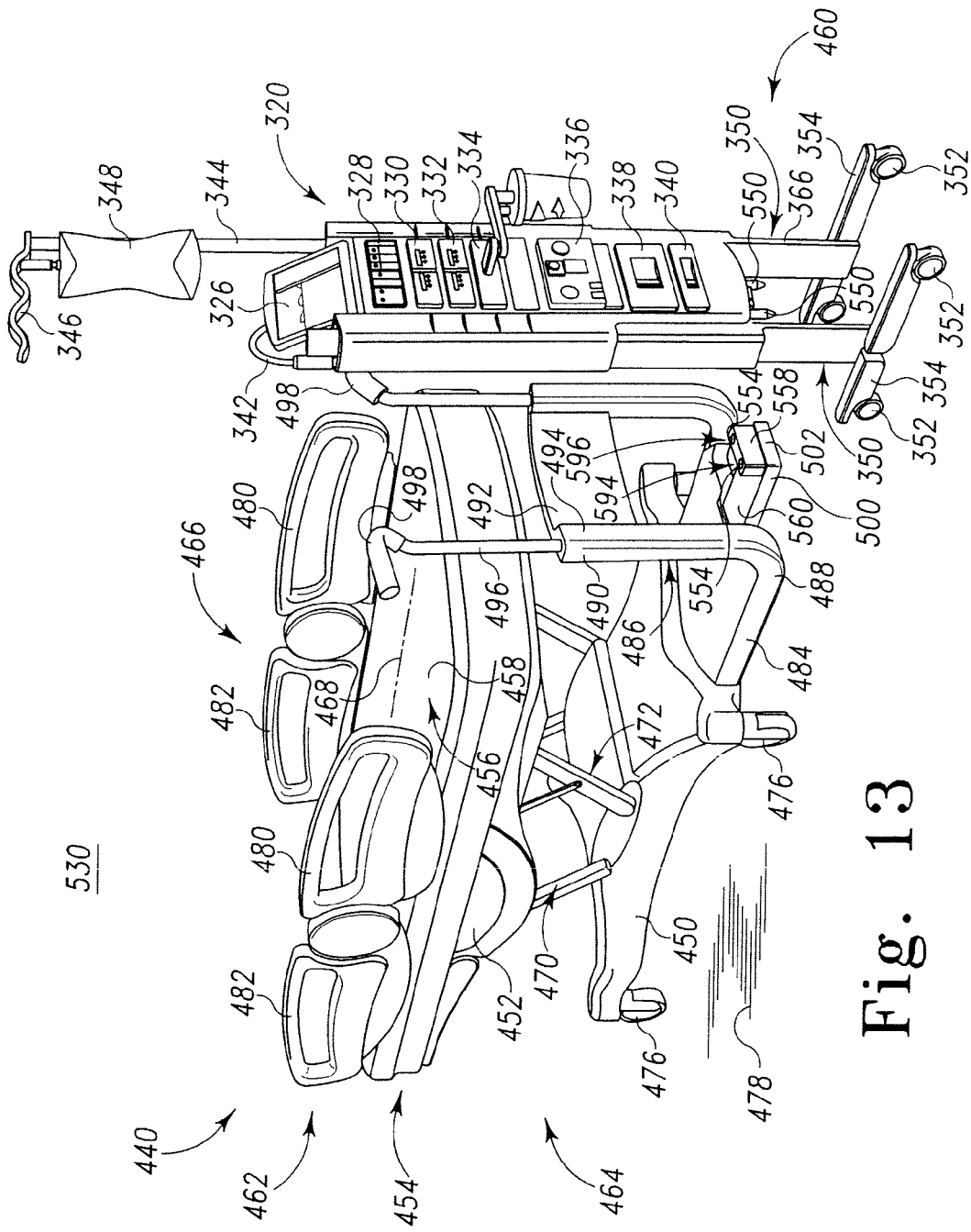
FIG. 13 is a perspective view showing the equipment support spaced from a head end of a hospital bed.
Figure 14:
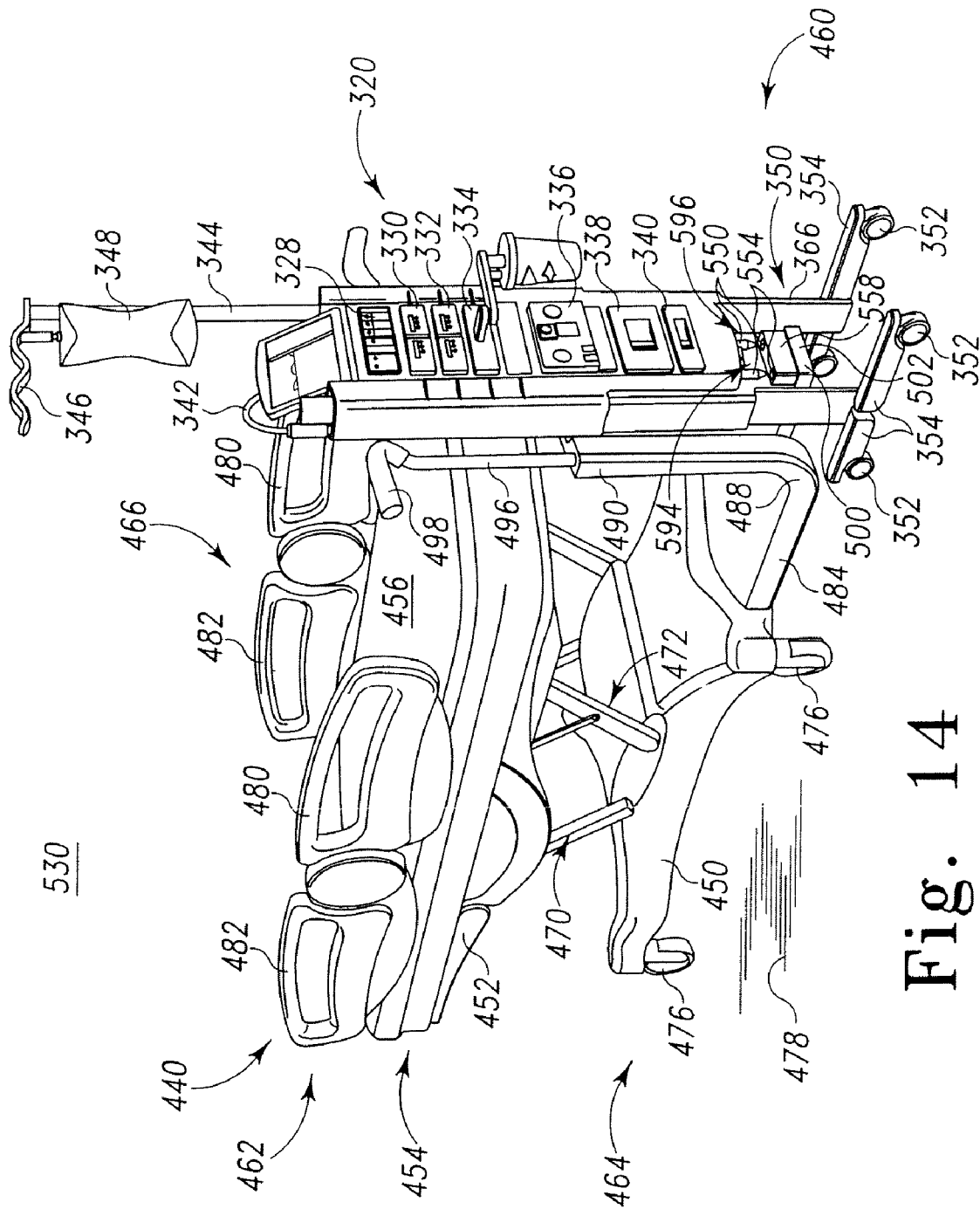
FIG. 14 is a perspective view showing the equipment support moved to a position having the main structure above a support ledge of the hospital bed and the legs of the equipment support on either side of the support ledge.

A push bar 496 extends vertically upwardly from a free end of each second portion 490 as shown, for example, in FIG. 13. Each push bar 496 has an outwardly-turned handle post 498 that may be grasped by a caregiver for moving the bed 440. In the illustrated embodiment, the handle posts 498 are enclosed in respective sleeves made from soft material, such as rubber. The push bars 496 and the associated handles 498 are located forward of a footprint of the upper frame 452 of the bed 440.

Still referring to FIG. 13, a second relatively narrow ledge 500 extends outwardly in a cantilevered manner from the head end 460 of the first relatively wide ledge 484. The ledge 500 is spaced from the floor 478. The ledge 500 is positioned intermediate of the push bars 496. At least a forward portion 502 of the ledge 500 extends outside the footprint of the upper frame 452. The equipment support 320 is detachably coupled to the forward portion 502 as shown in FIGS. 17, 18. In the illustrated example, the width of the equipment support 320 is less than the inner spacing between the vertically-extending portions 490 of the frame members 486 as shown in FIG. 13. In some embodiments, the width of the equipment support 320 is equal to the width of the base frame 450. In the illustrated example, the width of the ledge 500 is less than the inner spacing between the downwardly-extending support legs 350 of the equipment support 320. In some embodiments, the width of the ledge 500 is equal to the width of the equipment support 320.

When the equipment support 320 is coupled to the base frame 450 of the bed 440, an upper portion 504 of the equipment support 320 is situated above the upper frame 452 as shown in FIGS. 17, 18. Attachment of the equipment support 320 to the base frame 450, instead of the upper frame 452 of the bed 440, allows the equipment support 320 to be taller so that it can have multiple equipment-receiving cavities 322 for receiving multiple patient care modules 324.

As shown in FIG. 19, a telescopic column 520 is coupled to a distal end 522 of the support arm 442 by a coupler 524. A proximal end 526 of the support arm 442 is supported by a support structure 528 that extends upwardly from the floor 478 of a hospital room 530 in the illustrated embodiment. Alternatively, the proximal end 526 of the support arm 442 may be supported by a ceiling or a wall of the hospital room 530. The support arm 442 is pivotable about a vertical axis 532 extending through the proximal end 528. The illustrative support arm 442 is telescopic so that its distal end 522 telescopes horizontally relative to its proximal end 526.

Figures 20, 21:
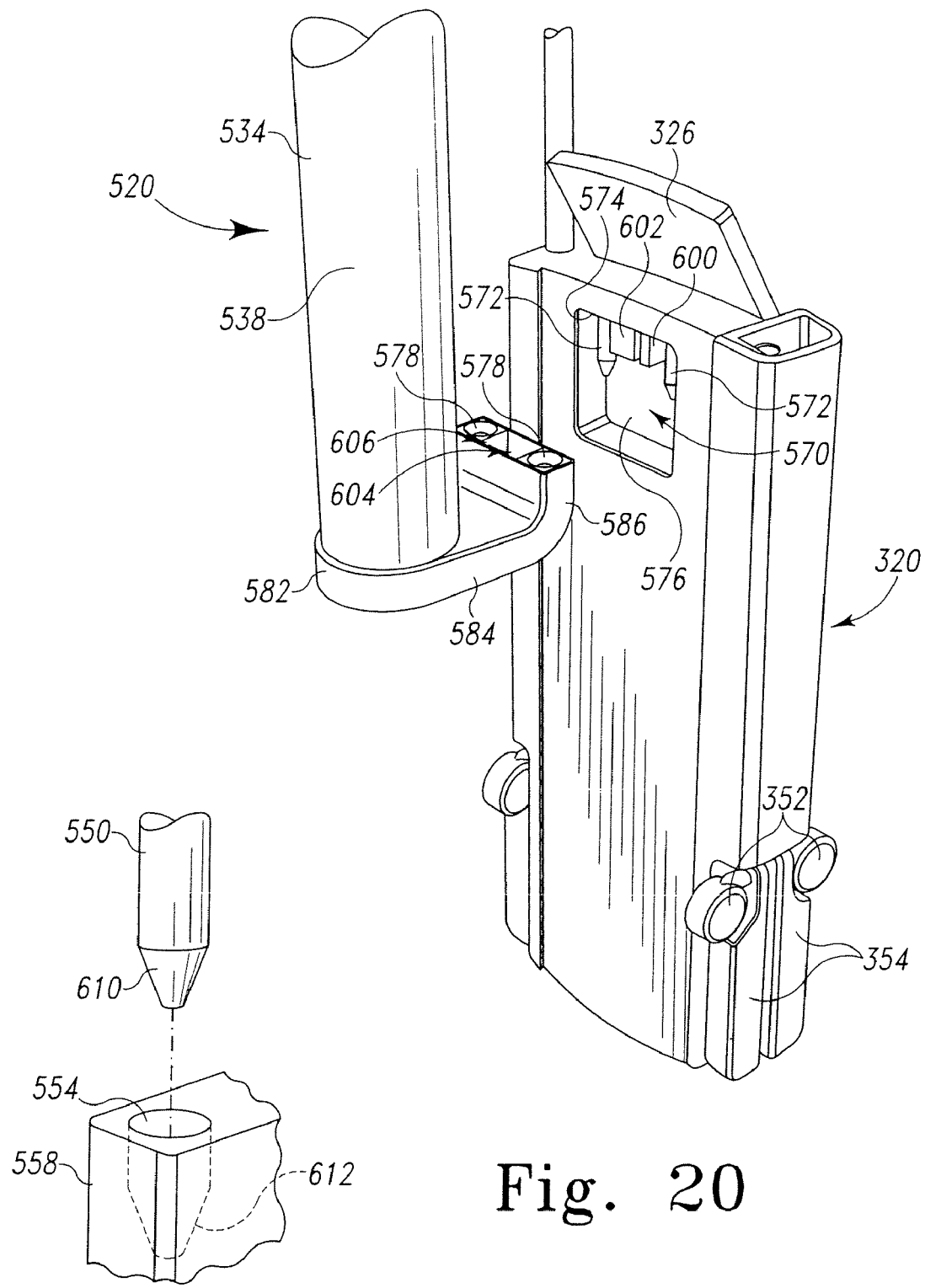
FIG. 20 is a perspective view showing a support member that is coupled to a lower region of the support arm aligned for insertion into the cavity of the main structure of the equipment support.
FIG. 21 is a perspective view showing a coupling pin extending downwardly from a bottom wall of the equipment support overlying an upwardly-opening socket extending upwardly from a top wall of a support structure of the bed as the equipment support is mated with the bed.

The column 520 has a lower portion 534 that telescopes vertically relative to an upper portion 536 under the power of an electric motor housed in the upper portion 536. Illustratively, the motor is a linear actuator of the type commercially available from the Linak Company of Denmark. It is understood that drivers such as hydraulic cylinders, magnetic cylinders, pneumatic cylinders, and the like may be used in lieu of the motor to cause vertical telescopic movement of the lower portion 534 of the column 520 relative to the upper portion 536. The motor is actuated by a control (not shown) positioned on the lower portion 534 of the column 520. Alternatively, the motor may be operated by a wired or wireless remote control or a control positioned on a wall of the hospital room 530. The equipment support 320 is detachably coupled to the lower portion 538 of the column 520 as shown in FIGS. 19, 20.

The vertical telescopic movement of the column 520 permits the equipment support 320 to be lifted off the bed 440 and lowered onto the floor 478 of the hospital room 530 as shown in FIGS. 6, 8, 9 and 12-14 for standalone operation thereof. Also, such telescopic movement of the column 520 permits the equipment support 320 to be lifted off the floor 478 and reattached to the bed 440 as shown in FIGS. 17, 18 or to the support arm 442 as shown in FIG. 19. The pivoting movement of the support arm 442 about the vertical axis 532, the horizontal telescoping movement of the support arm 442, and the vertical telescoping movement of the column 520 allow the equipment support 320 to be positioned at any desirable location within a range of movements. As previously indicated, the bed 440, the support arm 442, and the column 520 merely illustrate the environment for the operation of the equipment support 320.

As shown, for example, in FIG. 9, a pair of laterally-spaced coupling or locating pins 550 extend downwardly from the downwardly-facing wall 552 of the equipment support 320. The downwardly-extending pins 550 are configured for reception in a complementary pair of upwardly-opening sockets 554 of the hospital bed 440 as shown, for example, in FIG. 13. The upwardly-opening sockets 554 are received in respective socket-receiving openings formed in a mounting block 558. The mounting block 558 is secured to the upwardly-facing wall 560 of the forward portion 502 of the ledge 500 of the hospital bed 440. The lateral spacing between the upwardly-opening sockets 554 is the same as the lateral spacing between the downwardly-extending pins 550.

As shown in FIG. 12, a mounting block-receiving cavity or pocket 570 is formed in the upper region of the back wall 302 of the equipment support 320. A pair of laterally-spaced coupling or locating pins 572 extend downwardly beyond a downwardly-facing wall 574 of the cavity 570. The downwardly-extending pins 572 are spaced outwardly from a back wall 576 of the cavity 570. The downwardly-extending pins 572 are configured for reception in a complementary pair of upwardly-opening sockets 578 shown in FIG. 20. The upwardly-opening sockets 578 are received in respective socket-receiving openings formed in a mounting block 582 of the column 520. The mounting block 582 has a first portion 584 that extends outwardly in a cantilevered fashion from a lower region 538 of the lower portion 534 of the column 520. The mounting block 582 has a second lip portion 586 that extends upwardly from a distal end of the first portion 584.

The socket-receiving openings are formed in the upwardly-extending lip portion 586 of the mounting block 582.

The lateral spacing between the upwardly-opening sockets 578 of the column 520 is the same as the lateral spacing between the downwardly-extending coupling pins 572 of the equipment support 320. To attach the equipment support 320 to the column 520, the upwardly-extending lip portion 586 of the mounting block 582 is inserted into the mounting block-receiving cavity 570 and the lower portion 534 of the column 520 is raised so that the downwardly-extending pins 572 of the equipment support 320 are received in the upwardly-opening sockets 578. The lip portion 586 of the mounting block 582 is sized and shaped to facilitate reception thereof in the cavity 570 even when the alignment between the two is slightly off as the lip portion 586 of the column 520 is inserted into mounting block-receiving cavity 570. Thus, the width and the thickness of the second portion 586 of the mounting block 582 is slightly less than the width and the thickness of the cavity 570, respectively. The second portion 586 of the mounting block 582 tapers gently from, wide to narrow, in a forward direction away from the column 520.

Referring to FIG. 9, a power connector 590 (shown in FIG. 10) and a data connector 592 (shown in FIG. 11) are coupled to the downwardly-facing wall 552 of the equipment support 320 between the coupling pins 550. A complementary power connector 594 (shown in FIG. 10) and a complementary data connector 596 (shown in FIG. 11) are coupled to the mounting block 558 of the bed 440 between the upwardly-opening sockets 554. The power and data connectors 590, 592 of the equipment support 320 are configured to be coupled to the associated power and data connectors 594, 596 of the bed 440 when the equipment support 320 is coupled to the bed 440 as shown, for example, in FIGS. 15-18.

As shown in FIG. 12, a power connector 600 and a data connector 602 are coupled to the downwardly-facing wall 574 of the equipment support 320 between the downwardly-extending coupling pins 572. As shown in FIG. 20, a complementary power connector 604 and a complementary data connector 606 are coupled to the mounting block 582 of the column 520 between the upwardly-opening sockets 578. The power and data connectors 600, 602 of the equipment support 320 are configured to be coupled to the associated power and data connectors 604, 606 of the column 520 when the equipment support 320 is coupled to the column 520 as shown in FIG. 19.

In the illustrated embodiment, the two power connectors 590, 600, shown in FIGS. 9 and 12 respectively, coupled to the equipment support 320 are identical. Likewise, the power connectors 594, 604 coupled to the bed 440 and the column 520 are identical. Also, the two data connectors 592, 602, shown in FIGS. 9 and 12 respectively, coupled to the equipment support 320 are identical in the illustrated embodiment. Likewise, the data connectors 596, 606 coupled to the bed 440 and the column 520 are identical.

Illustratively, as shown in FIG. 21, the coupling pins 550, 572 each has a frustoconical tapered end portion 610 for facilitating engagement with a complementary upwardly-facing frustoconical opening 612 in the associated sockets 554, 578 even when the alignment between the two is slightly off as the equipment support 320 is lowered to engage the bed 440 or the lower portion 534 of the column 520 is raised to engage the equipment support 320. The tapered end portions 610 of the coupling pins 550, 572 vary in diameter from wide to narrow in a downward direction. It should be understood, however, that other approaches by which the bed 440 or the column 520 engage and support the equipment support 320 are within the scope of this disclosure. For example, the bed 440 could have a pair of upwardly-extending posts (not shown), while the equipment support 320 could have a pair of downwardly-opening sockets (not shown). The sockets 554, 578 are illustratively made from a different material than steel, such as brass or aluminum bronze, to allow the coupling pins 550, 572 of the equipment support 320 to be received in the associated sockets 554, 578 without galling the mating surfaces.

To attach the equipment support 320 to the bed 440, the equipment support 320 lowered onto the bed 440. The downwardly-extending coupling pins 550 of the equipment support 320 engage the associated upwardly-opening sockets 554 of the bed 440 before the power and data connectors 590, 592 of the equipment support 320 engage the respective power and data connectors 594, 596 of the bed 440 to align the power and data connectors 590, 592 of the equipment support 320 with the respective power and data connectors 594, 596 of the bed 440. As the engagement between the coupling pins 550 and the associated sockets 554 progresses, the power and data connectors 590, 592 couple to the respective power and data connectors 594, 596 to supply power to the equipment support 320 and to establish a communication link between the equipment support 320 and the bed 440. Also, the engagement between the coupling pins 550 and the sockets 554 mechanically secures the equipment support 320 to the bed 440.

To attach the equipment support 320 to the column 520, the column 520 approaches the back wall 302 of the equipment support 320. The upwardly-extending lip portion 586 of the mounting block 582 is inserted into the mounting block-receiving cavity 570 and the lower portion of 534 of the column 520 is then raised. The downwardly-extending coupling pins 572 of the equipment support 320 engage the associated upwardly-opening sockets 578 of the column 520 before the power and data connectors 600, 602 of the equipment support 320 engage the respective power and data connectors 604, 606 of the column 520 to align the power and data connectors 600, 602 of the equipment support 320 with the respective power and data connectors 604, 606 of the column 520. As the engagement between the coupling pins 572 and the associated sockets 578 progresses, the power and data connectors 600, 602 couple to the respective power and data connectors 604, 606 to supply power to the equipment support 320 and to establish a communication link between the equipment support 320 and the column 520. Also, the engagement between the coupling pins 572 and the sockets 578 mechanically secures the equipment support 320 to the column 520.

The power and data connectors 590, 592 and 600, 602 are arranged on the equipment support 320 so that the power and data connectors 594, 596 of the bed 440 and the power and data connectors 604, 606 of the column 520 can be coupled substantially simultaneously to the respective power and data connectors 590, 592 and 600, 602 of the equipment support 320 before disconnection of either one of the power and data connectors 594, 596 of the bed 440 and the power and data connectors 604, 606 of the column 520 from the respective power and data connectors 590, 592 and 600, 602 of the equipment support 320 to permit the equipment support 320 to be transferred between the bed 440 and the column 520 without a loss of power to the equipment support 320 or without a loss of communication link with the equipment support 320.

Likewise, the coupling pins 550, 572 are arranged on the equipment support 320 so that the sockets 554 of the bed 440 and the sockets 578 of the column 520 can be coupled substantially simultaneously to the respective coupling pins 550, 572 before disconnection of either one of the sockets 554 of the bed 440 and the sockets 578 of the column 520 from the respective coupling pins 550, 572. This assures that the equipment support 320 is firmly secured to the bed 440 before it is released from the column 520, and firmly secured to the column 520 before it is released from the bed 440.

Figure 7:
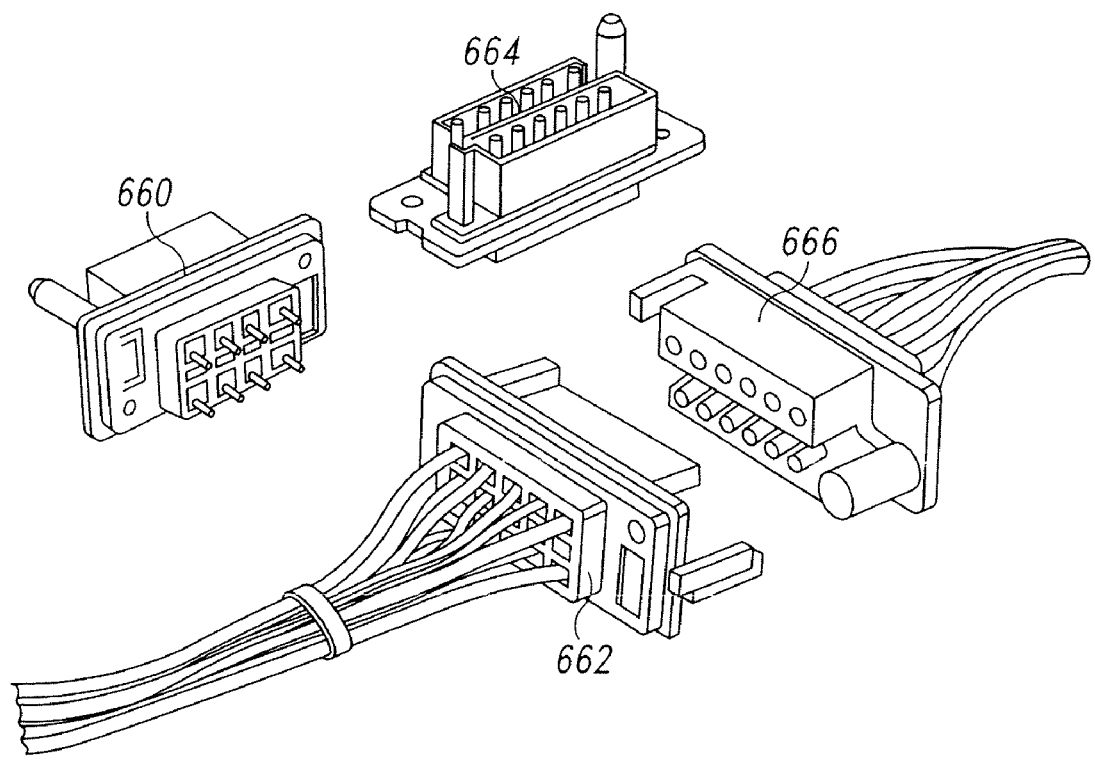
FIG. 7 is a perspective showing a combined power and data connector of the equipment support and a complementary power and data connector of a patient care equipment module.

Referring to FIG. 7, a power connector 660 and a data connector 662 are coupled to an equipment-support-facing wall of each patient care module 324. A complementary power connector 664 and a complementary data connector 666, also shown in FIG. 7, are coupled to a patient-care-module-facing wall of an associated equipment-receiving cavity 322 in the equipment support 320. The power and data connectors 660, 662 of each patient care module 324 are configured to be coupled to the respective power and data connectors 664, 666 in the associated equipment-receiving cavity 322 in the equipment support 320 to supply power to the module 324 and to establish a communication link between the module 324 and the equipment support 320 when the module 324 is received in the associated equipment-receiving cavity 322 in the equipment support 320 as shown in FIGS. 8, and 13-19.

Thus, each of the mini modules 328, the IV pump modules 330, 332, the suction module 334, the ventilator module 336, and the liquid oxygen module 338 have power and data connectors 660, 662 which are configured to be coupled to associated power and data connectors 664, 666 of the equipment support 320. The power and data connectors 664, 666 of the equipment support 320 are accessible for connection to the power and data connectors 660, 662 of the modules 324 through respective openings (not shown) in an interior wall of the equipment support 320.

In the illustrated embodiment, the data connector 596 of the bed 440, the data connector 606 of the column 520 and the two data connectors 592, 602 of the equipment support 320 each comprise a wireless coupler. The wireless couplers 592, 596, 602, 606 each comprise one or more of the following: a photoemitter, a photodetector, a photodiode, a radio frequency (RF) transmitter, an RF receiver, an RF transceiver, an infrared (IR) transmitter, an IR receiver, and an IR transceiver. Alternatively, wired data couplers may be used in lieu of the wireless data couplers 592, 596, 602, 606. Data from the patient care module 324 is wirelessly communicated to a computer network 690 of a healthcare system so that other computer devices connected to the computer network 690 have access to the data from the patient care module 324 when the patient care module 324 is received in the associated equipment-receiving cavity 322 in the equipment support 320 and the equipment support 320 is coupled to the bed 440 or the support arm 442.

The wireless communication between the patient care module 324 and the computer network 690 may be in accordance with any desired protocol, including the following protocols: IrDA, spread spectrum (including the Bluetooth protocol), RS232, TCP/IP, USB, and 802.11$_x$. The wireless communication may use frequency modulation or by frequency modulated infrared (FMIR). In some embodiments, data includes control signals for the operation of the patient care modules 324, the display 326 and the on-board microcontroller 692.

In the illustrated embodiment, the four power and data connectors 590, 592 and 600, 602 of the equipment support 320, the two power and data connectors 594, 596 of the bed 440 and the two power and data connectors 604, 606 of the support arm 442 are separate devices. Each of these separate power and data connectors 590, 592; 594, 596; 600, 602 and 604, 606 may be replaced with a combined power and data connector of the type illustrated in a PCT Pat. App. Pub. No. WO2005/022692, entitled "Plug and Receptacle Having Wired and Wireless Coupling," which is hereby incorporated by reference herein.

In some embodiments, the power and data connectors 660, 662 of the patient care module 324 and the power and data connectors 664, 666 of the equipment support 320 are drawer connectors to facilitate blind mating when the module 324 is inserted into the associated equipment-receiving cavity 322 of the equipment support 320. Such drawer connectors may be of the type illustrated in U.S. Pat. No. 4,664,456. In some embodiments, the power and data connectors 664, 666 of the equipment support 320 are receptacle connectors and the power and data connectors 660, 662 of the patient care module 324 are plug connectors. In some other embodiments, the power and data connectors 664, 666 of the equipment support 320 are plug connectors and the power and data connectors 660, 662 of the patient care modules 324 are receptacle connectors.

As shown in FIG. 22, the touchscreen display 326 is operable in several modes, either at the same time or at different times, when the equipment support 320 is coupled to the bed 440. In a first mode, the touchscreen display 326 is operable to display patient data. Illustratively, the patient data includes blood pressure, temperature, pulse rate, respiratory rate, blood oxygen saturation level, patient weight, and the like. This list is intended to be exemplary, not exhaustive, and it is contemplated by this disclosure that all types of patient data may be displayed on touchscreen display 326. In a second mode, the touchscreen display 326 is operable to display a first plurality of icons that are touchable to move the movable portions of the bed 440, such as the head, thigh and foot sections of the deck 454 and the side rails 480, 482. In a third mode, the touchscreen display 326 is operable to display a second plurality of icons that are touchable to provide input to the on-board microcontroller 692. In a fourth mode, the touchscreen display 326 is configured to display the operational status of the bed 440 including one or more of the following: bed function lock-outs, bed articulation, bed elevation, siderail positions, and therapy surface data. In a fifth mode, the touchscreen display 326 is configured to display the operational status of the patient care equipment 324 including information concerning one or more of the following: an alarm status, and equipment settings.

The on-board battery module 340, shown, for example, in FIG. 6, supplies power to the patient care modules 324, the display 326 and the on-board microcontroller 692. Alternatively, the bed 440 and the support arm 442 each has a power source, such as, for example, a battery 694 shown in FIG. 19 or a converter to convert a line voltage to a low DC voltage, for supplying power to the patient care modules 324, the display 326 and the microcontroller 692 when the equipment support 320 is coupled to the bed 440 or the column 520. The equipment support 320 has conductors for electrically coupling the patient care modules 324, the display 326 and the microcontroller 692 to the power and data connectors 590, 592 and 600, 602 of the equipment support 320. Conductors may also extend between the display 326, the on-board microcontroller 692 and the power and data connectors 662 of the equipment support 320.

Figure 23:
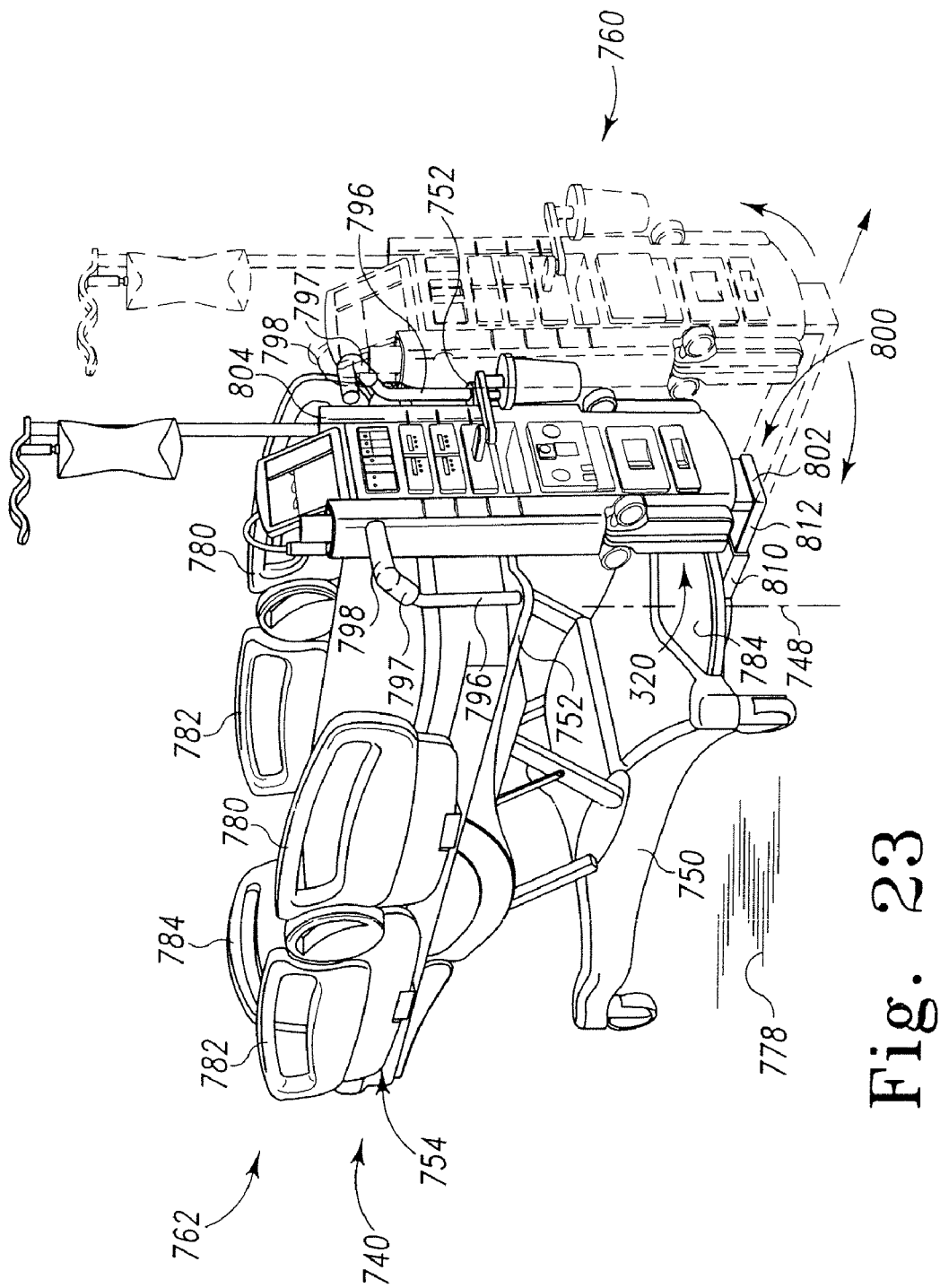
FIG. 23 is a perspective view showing a hospital bed having a swivelable forwardly-extending support structure for supporting the equipment support.
Figure 24:
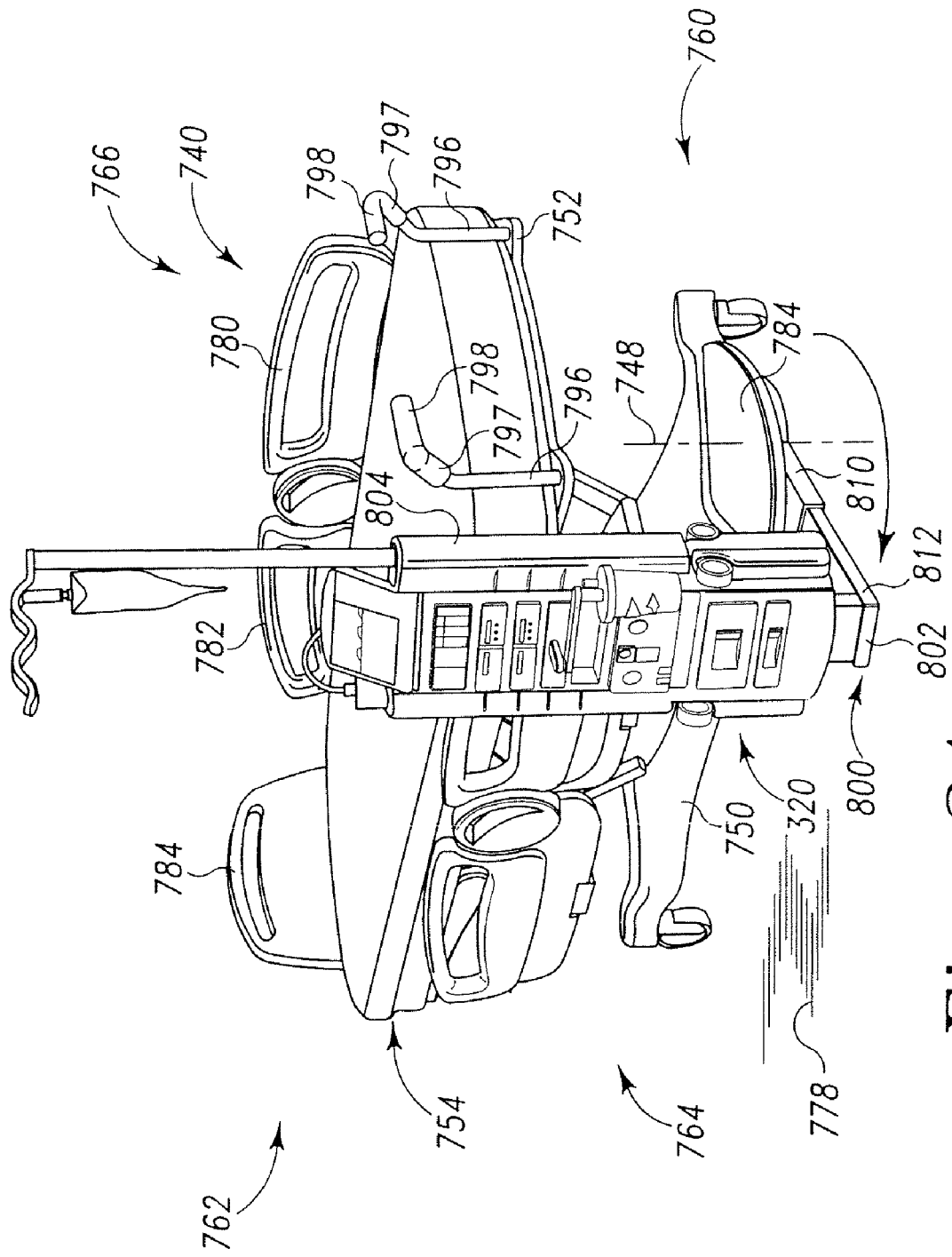
FIG. 24 is a perspective view, similar to FIG. 23, showing the equipment support swiveled to one side of the bed.

FIGS. 23 and 24 show a hospital bed 740 similar to the bed 440 shown in FIGS. 13-19, except that the bed 740 has a swivelable forwardly-extending support structure 800 for supporting the equipment support 320 so that the equipment support 320 can be swiveled to either side of the bed 740 as needed. Where appropriate, like reference numerals are used to denote portions of the bed 740 that are substantially similar to like portions of the bed 440. Thus, the bed 740 includes a base frame 750, an upper frame 752 supported above the base frame 750, and an articulating deck 754 supported above the upper frame 752. Two side rails 780 are coupled to the head section of the deck 754. Two side rails 782 are coupled to the upper frame 752 or to the foot section of the deck 754. A pair of push bars 796 are coupled to the upper frame 752 near the head end 760. Each push bar 796 has a forwardly and upwardly-extending portion 797 and an inwardly-extending portion 798 that forms a handle post.

A relatively wide ledge 784 extends forwardly in a cantilevered manner from the head end 760 of the base frame 750. In the illustrated example, the ledge 784 has an arcuate forwardly-facing wall which forms an arc of a circle having a center located on a vertical axis 748. In the illustrated example, the width of the ledge 784 is less than the width of the base frame 750. A relatively narrow support structure 800 extends forwardly in a cantilevered manner from the head end 760 of the relatively wide ledge 784. In the illustrated example, the support structure 800 is coupled to the underside of the ledge 784 for pivoting movement about the vertical axis 748. Both the ledge 784 and the swivelable support structure 800 are spaced from the floor 778 of the hospital room. At least a forward portion 802 of the swivelable support structure 800 extends outside the footprint of the upper frame 752. As shown in FIGS. 23, 24, the equipment support 320 is detachably coupled to the forward portion 802 of the swivelable support structure 800 in a manner similar to the manner in which the equipment support 320 is detachably coupled to the forward portion 502 of the relatively narrow ledge 500 as shown, for example, in FIGS. 17 and 18.

In the illustrated example, the support structure 800 is telescopic so that, when attached, the equipment support 320 can move between a retracted position closer to the bed 740 where the equipment support 320 is located between the handle posts 798 as shown in solid in FIG. 23 and an extended position further spaced from the bed 740 where the equipment support 320 is located forwardly of the handle posts 798 as shown in phantom in FIG. 23 so that the equipment support 320 can clear the handle posts 798 when it is swiveled to a side of the bed 740. In such embodiments, to move the equipment support 320 to a side of the bed 740, the equipment support 320 is first moved to the extended position forwardly of the handle posts 798 and then moved to one of the two sides of the bed 740 as desired. The telescopic support structure 800 includes a first segment 810 and a second segment 812 that telescopes horizontally into and out of the first segment 810. In some alternate embodiments, the support structure 800 is not telescopic, but it is dimensioned such that the equipment support 320, when attached to the support structure 800, is positioned forwardly of the handle posts 798 so that it can swivel from side to side without interference from the handle posts 798.

In the illustrated example, the width of the equipment support 320 is less than the inner spacing between the handle posts 798. In some embodiments, the width of the equipment support 320 is equal to the width of the base frame 750. In the illustrated example, the width of the swivelable support structure 800 is less than the inner spacing between the downwardly-extending support legs 350 of the equipment support 320. In some embodiments, the width of the support structure 800 is equal to the width of the equipment support 320. When the equipment support 320 is supported by the base frame 750 of the bed 740, an upper portion 804 of the equipment support 320 is situated above the upper frame 752 as shown in FIGS. 23, 24. Attachment of the equipment support 320 to the base frame 750, instead of the upper frame 752, allows the equipment support 320 to be taller so that it can have multiple equipment-receiving cavities 322 for receiving multiple patient care modules 324.

While the features or aspects of various inventions have been illustrated and described in detail in the foregoing drawings and description, the same is to be considered as illustrative and not restrictive in character, it being understood that only illustrative embodiments thereof have been shown and described and that all changes and modifications that come within the spirit of the respective inventions are desired to be protected.

The invention claimed is:

1. A patient care equipment support for use with patient care equipment having power and data connectors, the equipment support comprising power and data connectors configured to be coupled to the respective power and data connectors of the patient care equipment when the patient care equipment is coupled to the equipment support to provide a power coupling and a data coupling between the patient care equipment and the equipment support, wherein the equipment support includes at least one equipment-receiving cavity and the power and data connectors of the patient care equipment are coupled to the respective power and data connectors of the equipment support when the patient care equipment is received in the at least one equipment-receiving cavity, wherein the power and data connectors of the equipment support and the patient care equipment are drawer connectors to facilitate blind mating when the patient care equipment is inserted into the associated equipment-receiving cavity of the equipment support.

2. The equipment support of claim 1, wherein the patient care equipment comprises any one or more of the following: an infusion pump, a ventilator, a cardiac monitor, a pulse oximeter, a non-invasive blood pressure measuring device, a digital thermometer, a liquid oxygen module, a defibrillator, a respiratory rate measuring device, medical gas delivery equipment, intra-venous bags, and the like.

3. The equipment support of claim 1, further comprising any one or more of the following: a microcontroller, a user interface device, a display, an on-board battery, and the like.

4. The equipment support of claim 1, comprising an on-board battery to supply power to the patient care equipment when the patient care equipment is coupled to the equipment support.

5. The equipment support of claim 1, wherein the equipment support is configured to be detachably coupled to a first device, the equipment support comprising extendible support legs with floor-engaging wheels which allow the equipment support to be decoupled from the first device and supported on an underlying floor for independent operation thereof.

6. The equipment support of claim 5, wherein the support legs are configured to retract when the equipment support is lifted off the floor and coupled to the first device.

7. The equipment support of claim 1, wherein the equipment support is transferable between a first device and a second device.

8. The equipment support of claim 7, wherein the first device has first power and data connectors, the equipment support has third power and data connectors, the equipment support is configured to be detachably coupled to the first device so that the third power and data connectors couple to the respective first power and data connectors to supply power to the equipment support and to establish a communication link between the first device and the equipment support.

9. The equipment support of claim 8, wherein the communication link between the first device and the equipment support is wireless.

10. The equipment support of claim 8, wherein the second device has second power and data connectors, the equipment support has fourth power and data connectors, the equipment support is configured to be detachably coupled to the second device so that the fourth power and data connectors couple to the respective second power and data connectors to supply power to the equipment support and to establish a communication link between the second device and the equipment support.

11. The equipment support of claim 10, wherein the communication link between the second device and the equipment support is wireless.

12. The equipment support of claim 7, wherein the first device is one of the following: a wall of a hospital room, a patient support, a hospital bed, a stretcher, a surgery table, and an ambulatory care chair.

13. The equipment support of claim 7, wherein the second device is one of the following: a support arm, a column, a headwall, a cart, and a stand.

14. The equipment support of claim 1, wherein the at least one equipment-receiving cavity comprises a plurality of equipment-receiving cavities, and each equipment-receiving cavity is configured to receive an associated patient care equipment.

15. The equipment support of claim 1, wherein the power and data connectors of the equipment support are receptacle connectors and the power and data connectors of the patient care equipment are plug connectors.

16. The equipment support of claim 1, wherein each power connector includes a wired coupler to supply electrical power to the patient care equipment, and each data connector includes a wireless coupler to establish a communication link between the patient care equipment and the equipment support.

17. The equipment support of claim 16, wherein the wired coupler comprises electrical contacts.

18. The equipment support of claim 17, wherein the wireless coupler comprises one or more of the following: a photoemitter, a photodetector, a photodiode, a radio frequency (RF) transmitter, an RF receiver, an RF transceiver, an infrared (IR) transmitter, an IR receiver, and an IR transceiver.

19. The equipment support of claim 16, wherein data from the patient care equipment is wirelessly communicated to a computer network of a healthcare system when the patient care equipment is coupled to the equipment support so that other computer devices connected to the computer network have access to the data from the patient care equipment.

20. The equipment support of claim 16, wherein wireless communication between the patient care equipment and the equipment support is in accordance with one of the following protocols: IrDA, spread spectrum (including the Bluetooth protocol), RS232, TCP/IP, USB, and 802.11$_x$.

21. The equipment support of claim 16, wherein wireless communication between the patient care equipment and the equipment support uses frequency modulation.

22. The equipment support of claim 16, wherein wireless communication between the patient care equipment and the equipment support uses frequency modulated infrared (FMIR).

23. A patient care equipment support for use with patient care equipment having power and data connectors, the equipment support comprising power and data connectors configured to be coupled to the respective power and data connectors of the patient care equipment when the patient care equipment is coupled to the equipment support to provide a power coupling and a data coupling between the patient care equipment and the equipment support, wherein the equipment support is transferable between a first device and a second device, wherein the first device has first power and data connectors, the equipment support has third power and data connectors, the equipment support is configured to be detachably coupled to the first device so that the third power and data connectors couple to the respective first power and data connectors to supply power to the equipment support and to establish a communication link between the first device and the equipment support, wherein the second device has second power and data connectors, the equipment support has fourth power and data connectors, the equipment support is configured to be detachably coupled to the second device so that the fourth power and data connectors couple to the respective second power and data connectors to supply power to the equipment support and to establish a communication link between the second device and the equipment support, wherein the third and the fourth power and data connectors are arranged so that the first and second power and data connectors can be coupled substantially simultaneously to the respective third and fourth power and data connectors before disconnection of either one of the first and second power and data connectors from the respective third and fourth power and data connectors to permit the equipment support to be transferred between the first and second devices without a loss of power to the equipment support or without a loss of communication link with the equipment support.

* * * * *